(12) United States Patent
Padmanabhan et al.

(10) Patent No.: US 8,071,051 B2
(45) Date of Patent: Dec. 6, 2011

(54) PORTABLE SAMPLE ANALYZER CARTRIDGE

(75) Inventors: Aravind Padmanabhan, Plymouth, MN (US); James A. Cox, New Brighton, MN (US); Cleopatra Cabuz, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 1104 days.

(21) Appl. No.: 10/908,460

(22) Filed: May 12, 2005

(65) Prior Publication Data

US 2005/0255600 A1    Nov. 17, 2005

Related U.S. Application Data

(60) Provisional application No. 60/571,235, filed on May 14, 2004.

(51) Int. Cl.
*B01L 3/00* (2006.01)
*C12M 1/34* (2006.01)

(52) U.S. Cl. .................................. 422/502; 435/288.7

(58) Field of Classification Search .............. 422/502; 435/288.7
See application file for complete search history.

(56) References Cited

U.S. PATENT DOCUMENTS

| | | | |
|---|---|---|---|
| 3,822,095 A | 7/1974 | Hirschfeld | |
| 3,830,569 A * | 8/1974 | Meric | 356/39 |
| 3,928,094 A | 12/1975 | Angell | |
| 3,976,862 A | 8/1976 | Curbelo | |
| 4,185,964 A * | 1/1980 | Lancaster | 436/17 |
| 4,199,471 A * | 4/1980 | Louderback et al. | 436/11 |
| 4,284,412 A | 8/1981 | Hansen et al. | |
| 4,478,076 A | 10/1984 | Bohrer | |
| 4,478,077 A | 10/1984 | Boher | |
| 4,501,144 A | 2/1985 | Higashi et al. | |
| 4,599,000 A | 7/1986 | Yamada | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 4,980,292 A | 12/1990 | Elbert et al. | |
| 5,017,497 A | 5/1991 | de Grooth et al. | |

(Continued)

FOREIGN PATENT DOCUMENTS

DE        10122321        4/2002

(Continued)

OTHER PUBLICATIONS http://www.micronics.net/tsensor.htm, pp. 1-4, downloaded Jun. 14, 2000.

(Continued)

*Primary Examiner* — Lore Jarrett

(74) *Attorney, Agent, or Firm* — Seager, Tufte & Wickhem LLC

(57) ABSTRACT

A sample analyzer cartridge for use at a point of care of a patient such as in a doctor's office, in the home, or elsewhere in the field. By providing a removable and/or disposable cartridge with all of the needed reagents and/or fluids, the sample analyzer can be reliably used outside of the laboratory environment, with little or no specialized training.

1 Claim, 12 Drawing Sheets

U.S. PATENT DOCUMENTS

| | | | |
|---|---|---|---|
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,262,302 A * | 11/1993 | Russell | 435/7.24 |
| 5,323,999 A | 6/1994 | Bonne et al. | |
| 5,425,921 A * | 6/1995 | Coakley et al. | 422/102 |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,837,547 A | 11/1998 | Schwartz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerie et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 * | 5/2002 | Cabuz et al. | 137/10 |
| 6,437,551 B1 | 8/2002 | Krulevitch et al. | |
| 6,506,609 B1 * | 1/2003 | Wada et al. | 436/148 |
| 6,537,501 B1 * | 3/2003 | Holl et al. | 422/101 |
| 6,549,275 B1 | 4/2003 | Cabuz et al. | |
| 6,597,438 B1 | 7/2003 | Cabuz et al. | |
| 6,712,925 B1 | 3/2004 | Holl et al. | |
| 7,420,659 B1 * | 9/2008 | Cabuz et al. | 356/39 |
| 7,497,997 B2 | 3/2009 | Glezer et al. | |
| 2003/0027225 A1 * | 2/2003 | Wada et al. | 435/7.21 |
| 2003/0030783 A1 | 2/2003 | Roche et al. | |
| 2003/0057968 A1 | 3/2003 | Wang et al. | |
| 2003/0096430 A1 | 5/2003 | Holl et al. | |
| 2003/0142291 A1 | 7/2003 | Padmanabhan et al. | |
| 2003/0159999 A1 | 8/2003 | Oakey et al. | |
| 2003/0199894 A1 * | 10/2003 | Boecker et al. | 606/181 |
| 2004/0019300 A1 * | 1/2004 | Leonard | 600/584 |
| 2004/0065143 A1 | 4/2004 | Husher | |
| 2004/0109386 A1 | 6/2004 | Gold et al. | |
| 2004/0154933 A1 | 8/2004 | Cosofret | |
| 2004/0233424 A1 | 11/2004 | Lee et al. | |
| 2005/0105077 A1 | 5/2005 | Padmanabhan et al. | |

FOREIGN PATENT DOCUMENTS

| | | |
|---|---|---|
| EP | 0269076 | 6/1988 |
| EP | 0694784 | 1/1996 |
| EP | 1001326 | 5/1999 |
| EP | 1134548 | 9/2001 |
| EP | 1359419 | 5/2003 |
| JP | 60082865 | 12/1983 |
| JP | 61066947 | 4/1986 |
| JP | 10073528 | 8/1996 |
| JP | 2000056228 | 7/1999 |
| JP | 2004257756 | 9/2004 |
| WO | WO 95/27199 | 3/1995 |
| WO | WO 99/60397 | 4/1999 |
| WO | WO 01/09598 | 7/2000 |
| WO | WO 02/10713 A2 | 2/2002 |
| WO | WO 02/10713 A3 | 2/2002 |
| WO | WO 02/10714 | 2/2002 |
| WO | WO 02/082057 | 10/2002 |
| WO | WO 2004/018967 | 3/2004 |
| WO | 2004059316 | 7/2004 |
| WO | 2005090983 | 9/2005 |
| WO | 2005108963 | 11/2005 |
| WO | 2005114142 | 12/2005 |
| WO | 2005114144 | 12/2005 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using a Prototype Microfluidics-Based Hematology Analyzer", SPIE Biomedical Optics 97, 1997.

Altendorf et al., "Differential Blood Cell Counts Obtained Using a Microchannel Based Flow Cytometer", Solid State Sensors & Actuators, vol. 1, 531, 1997.

Altendorf et al., "Implementation of Novel Optical Detection Methods for Clinically Important Blood Analytes Using Microfabricated Flow Structures (T-Sensors™)", MicroTAS 98, Banff, Canada, Apr. 1998.

Altendorf et al., "Microfabrication Technology for Research and Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.

Darling et al., "Integration of Microelectrodes With Etched Microchannels for In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Gwo-Bin Lee et al., "Multi-Cell-Line Micro Flow Cytometers with Buried SU-8/SOG Optical Waveguides Category: Optical MEMS," IEEE, pp. 503-506, 2002.

Hatch et al., "Microfluidic Approaches to Immunoassays", SPIE conference on Micromachining and Microfabrication Symposium at Santa Clara, CA, Sep. 20-22, 1999.

Huang et al., "Development of a Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3$^{rd}$ International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/ Sheraton Kauai Resort, Kauai, Hawaii, Aug. 21-24, 2000, 2 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, 2000, pp. 101-104.

Weigh et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation and Detection", Science, vol. 283, pp. 346-347, Jan. 15, 1999.

Weigl et al, "Optical and Electrochemical Diffusion-Based Detection of Analytes in Complex Samples Using Microfabricated Flow Structures (T-SensorSTM)", Micro- and nanofabn'cated electro-optical mechanical systems for biomedical and environmental applications II—SPIE vol. 3606, Jan. 25-26, 1999.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection in Silicon Flow Structures", B. Weigl et al., Analytical Methods & Instrumentation, µTTAS 96 special edition, 1996.

Weigl et al., "Design and Rapid Prototyping of Thin-Film Laminate-Based Microfluidic Devices," Biomedical Microdevices, vol. 3, No. 4, pp. 267-274, 2001.

"Guidance for Clinical Laboratory Improvement Amendments of 1988 (CLIA) Criteria for Waiver; Draft Guidance for Industry and FDA," Center for Devices and Radiological Health, US Dept. of Health and Human Services, 26 pages, Mar. 1, 2001.

Weigl et al., "Fluorescence and Absorbance Analyte Sensing in Whole Blood and Plasma Based on Diffusion Separation in Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, 207-212, 1998.

Yager et al., "Design of Microfluidic Sample Preconditioning Systems for Detection of Biological Agents in Environmental Samples", Yager, M. et al., SPIE Proceedings, 3515, 252-259, 1998.

HemoCue Hb 201+, Operating Manual, pp. 1-41, prior to Dec. 2006.

Lamvik et al., Nonlabeled Secondary Antibodies Augment/Maintain the Binding of Primary, Specific Antibodies to Cell Membrande Antigens, Cytometery 45, pp. 187-193, 2001.

* cited by examiner

PORTABLE SAMPLE ANALYZER CARTRIDGE

This application claims priority to provisional patent application Ser. No. 60/571,235 filed May 14, 2004, which is relied on and incorporated herein by reference.

BACKGROUND

The present invention generally relates to sample analyzers, and more particular, to sample analyzers and cartridges that can be used at the point of care of a patient, such as in a doctor's office, in the home, or elsewhere in the field.

Particle discrimination methods are useful in a variety of clinical assays, such as in determining the number and types of cells in a blood sample, detecting bacterial or virus particles in a body fluid sample, and assaying cell volumes and density. Detection of non-cellular particles, such as proteins and analyte in for example, a urine sample, is also valuable in certain clinical tests. Analysis of crystals and other particles in fluid suspension also has important industrial uses.

One method which allows rapid and efficient particle discrimination in a particle-suspension sample is flow cytometry. In this method, a suspension of particles, typically cells in a blood sample, is transported through a flow channel where the individual particles in the sample are illuminated with one or more focused light beams. The interaction of the light beam(s) with the individual particles flowing through the flow channel is detected by one or more light detectors. Commonly, the detectors are designed to measure light absorption or fluorescence emission, at specific beam or emission wavelengths, and/or light scattering at specific scattering angles. Thus, each particle that passes through the flow channel can be characterized as to one or more features related to its absorption, fluorescence, light scattering or other optical or electrical properties. The properties that are measured by the detectors may allow each particle to be mapped into a feature space whose axes are the light intensities or other properties which are measured by the detectors. In the ideal, the different particles in the sample map into distinct and non-overlapping regions of the feature space, allowing each particle to be analyzed based on its mapping in the feature space. Such analysis may include counting, identifying, quantifying (as to one or more physical characteristics) and/or sorting of the particles.

Two general types of light scattering measurements are routinely made in flow cytometry. Light intensity measurements made at small angles (about 1.5-13 degrees with respect to the incident light beam), usually called forward or small-angle scattering, give information on cell size. Forward scattering also strongly depends on the difference of refraction between cells and the extra-cellular medium, so that cells with damaged membranes, for example, can be distinguished. Light intensity measurements made at an angle of about 65 degrees-115 degrees from the incident light, usually referred to as orthogonal or large angle scattering, can provide information about the size and degree of structure of particles.

Simultaneous light scattering measurements at different angles or in combination with absorption or fluorescence measurements have been proposed in flow cytometry methods. For example, absorption of light in combination with light scattering can be used in flow cytometry to distinguish between erythrocytes and thrombocytes, and between lymphocytes, monocytes, basophilic granulocytes, eosinophilic granulocytes, and neutrophilic granulocytes. However, this method sometimes requires staining of the cells, and is therefore rather complex and may preclude using the cells for further study after cell sorting.

Light scattering measurements combined with circular dichroism (CD) and optical rotatory dispersion (ORD) also have the potential for particle discrimination in suspensions of virus particles or cells. Studies of the effect of Mie (isotropic particle) scattering on the CD and ORD spectra of DNA in viral particles suggest that scattering measurements can be used to correct ORD and CD measurements in larger biological structures, such as virus particles and cells, to allow particle discrimination on the basis of characteristic ORD and CD characteristics. Differential scattering of right and left circularly polarized light, for discrimination of a number of different microorganisms, has also been demonstrated. The circular intensity differential scattering (CIDS) method is like CD, which exploits the differential absorption of left and right circularly polarized light, but takes advantage of differential scattering by helical structures, such as DNA, of right and left circularly polarized light.

Typically, such particle discrimination methods are implemented, at least in part, using one or more pieces of equipment, collectively herein called a sample analyzer. Many sample analyzers are rather large devices that are used in a laboratory environment by trained personnel. To use many sample analyzers, a collected sample must first be processed, such as by diluting the sample to a desired level, adding appropriate reagents, centrifuging the sample to provide a desired separation, etc., prior to providing the prepared sample to the sample analyzer. To achieve an accurate result, such sample processing must typically be performed by trained personnel, which can increase the cost and time required to perform the sample analysis.

Many sample analyzers also require operator intervention during the analysis phase, such as requiring additional information input or additional processing of the sample. This can further increase the cost and time required to perform a desired sample analysis. Also, many sample analyzers merely provide raw analysis data as an output, and further calculations and/or interpretation must often be performed by trained personnel to make an appropriate clinical decision.

SUMMARY

The present invention generally relates to sample analyzers, and more particular, to sample analyzers with removable and/or disposable cartridges for use at the point of care of a patient such as in a doctor's office, in the home, or elsewhere in the field. By providing a removable and/or disposable cartridge with all of the needed reagents and/or fluids, the sample analyzer can be reliably used outside of the laboratory environment, with little or no specialized training. This may, for example, help streamline the sample analysis process, reduce the cost and burden on medical or other personnel, and increase the convenience of sample analysis for many patients, including those that require relatively frequent blood monitoring/analysis.

In one illustrative embodiment of the present invention, a sample analyzer is provided that has a removable cartridge that receives a collected sample, such as a collected whole blood sample, and once the removable cartridge is installed and the analyzer is activated, the analyzer and cartridge automatically processes the sample and the analyzer provides sufficient information for the user to make a clinical decision. In some embodiments, the analyzer displays or prints out quantitative results (e.g. inside and/or outside of a predefined range), such that no further calculations or interpretation is required by the user.

The sample analyzer may be used to, for example, determine the number and/or types of cells in a blood sample, detect bacterial or virus particles in a fluid, food or other sample, and/or assay cell volumes and densities in a sample. The sample analyzer may also be used for detection of non-cellular particles, such as uric acid crystals in a urine sample, as well as crystals and other particles in fluid suspension, and/or for any other suitable type of analysis, as desired.

In one illustrative embodiment, the analyzer includes a housing and a removable fluidic cartridge, wherein the housing is adapted to receive the removable fluidic cartridge. In some cases, the removable fluidic cartridge is a disposable cartridge. In one illustrative embodiment, the removable fluidic cartridge may include one or more reagents (e.g. lysing reagents, sphering reagents, dilutent, etc.), one or more analysis channels, one or more flow sensors, one or more valves, and/or a fluidic circuit that is adapted to process (e.g. lyse, sphere, dilute, mix, etc.) a sample and deliver processed sample(s) to the appropriate analysis channels on the cartridge. To support the card, the housing may include, for example, a pressure source, one or more light sources, one or more light detectors, a processor and a power source. The pressure source may provide appropriate pressure(s) to the removable fluidic cartridge ports to drive the fluids as required through the fluidic circuit. The one or more light sources of the analyzer may be used to interrogate the prepared sample in at least selected analysis channels of the removable cartridge, and the one or more light detectors of the analyzer may detect the light that passes through, is absorbed by and/or is scattered by the sample. The processor may be coupled to at least some of the light sources and detectors, and may determine one or more parameters of the sample. In some embodiments, the one or more analysis channels on the removable fluidic cartridge may include one or more flow cytometry channels and/or one or more absorption channels, but this is not required in all embodiments.

In some illustrative embodiments, a whole blood sample may be provided to the removable fluidic cartridge, and the removable cartridge may be adapted to perform a blood analysis, such as a complete blood count (CBC) analysis. To count and classify, for example, the red blood cells in the whole blood sample, a portion of the whole blood sample may be partitioned and provided to a red blood cell measurement channel in the removable cartridge. The portion of the blood sample that is provided to the red blood cell measurement channel may be diluted if desired, the red blood cells may be sphered on the fly, the resulting sample may be hydrodynamically focused for core formation and ultimately provided to a first cytometry channel in the removable cartridge.

In some cases, the first cytometry channel may be located along or under a first transparent flow stream window in the removable cartridge so that the cells/platelets in the flow stream may be optically interrogated by a first light source and a first light detector. A flow sensor may also be provided on the removable cartridge to provide a measure of the flow rate through the first cytometry channel.

In some cases, the measured parameters may include, for example, sample flow rate (FR), measurement time (T) duration, sample dilution factor (DF), number of red blood cells counted ($N_{RB}$), number of platelets counted ($N_{Plt}$), the diameter of each cell (drbc) and hemoglobin concentration of each cell (CHC). From these parameters, a number of red blood cell analysis parameters may be calculated including, for example, a red blood cell count (RBC), a platelet count (Plt), a mean cell hemoglobin concentration (MCHC), a mean cell volume (MCV), a mean cell hemoglobin content (MCH), a relative distribution width (RDW), a Hematocrit parameter (Hct) and/or a hemoglobin concentration (Hb).

In some embodiments, some of the blood sample may also be directed to an absorption measurement channel on the removable cartridge. The absorption measurement channel may be located along a transparent window so that the blood sample can be optically interrogated by a corresponding light source and light detector. Another flow sensor may be provided on the removable cartridge, if desired, to provide a measure of the flow rate into or through the absorption measurement channel, but this is not required. The absorption channel may be used to measure the absorption level of the incident light. The absorption level may provide, for example, a measure of the mean or bulk cell hemoglobin concentration in the blood sample.

To count and classify white blood cells, a portion of the whole blood sample may be partitioned and provided to a white blood measurement channel in the removable cartridge. The blood sample provided to the white blood measurement channel may be, for example, diluted if desired, the red blood cells may be lysed on the fly, the resulting sample may be hydrodynamically focused for core formation and ultimately provided to a second cytometry channel. The second cytometry channel may also be located along or under a transparent flow stream window of the removable cartridge so that the cells in the flow stream can be optically interrogated by a corresponding light source and detector. In some cases, a flow sensor may be provided on the removable cartridge to provide a measure of the flow rate through the second cytometry channel.

In some cases, illustrative measured parameters of the white blood cell measurement channel may include, for example, three (3) or (5) part white cell differentiation, total white blood cell count and/or on-axis white blood cell volume. Other parameters may also be measured or calculated, depending on the desired application. In some cases, stains and/or fluorescent tags may be added to the sample prior to providing the sample to the second cytometry channel, which in some cases, may aid in cell differentiation.

BRIEF DESCRIPTION

DESCRIPTION

Figure 1:
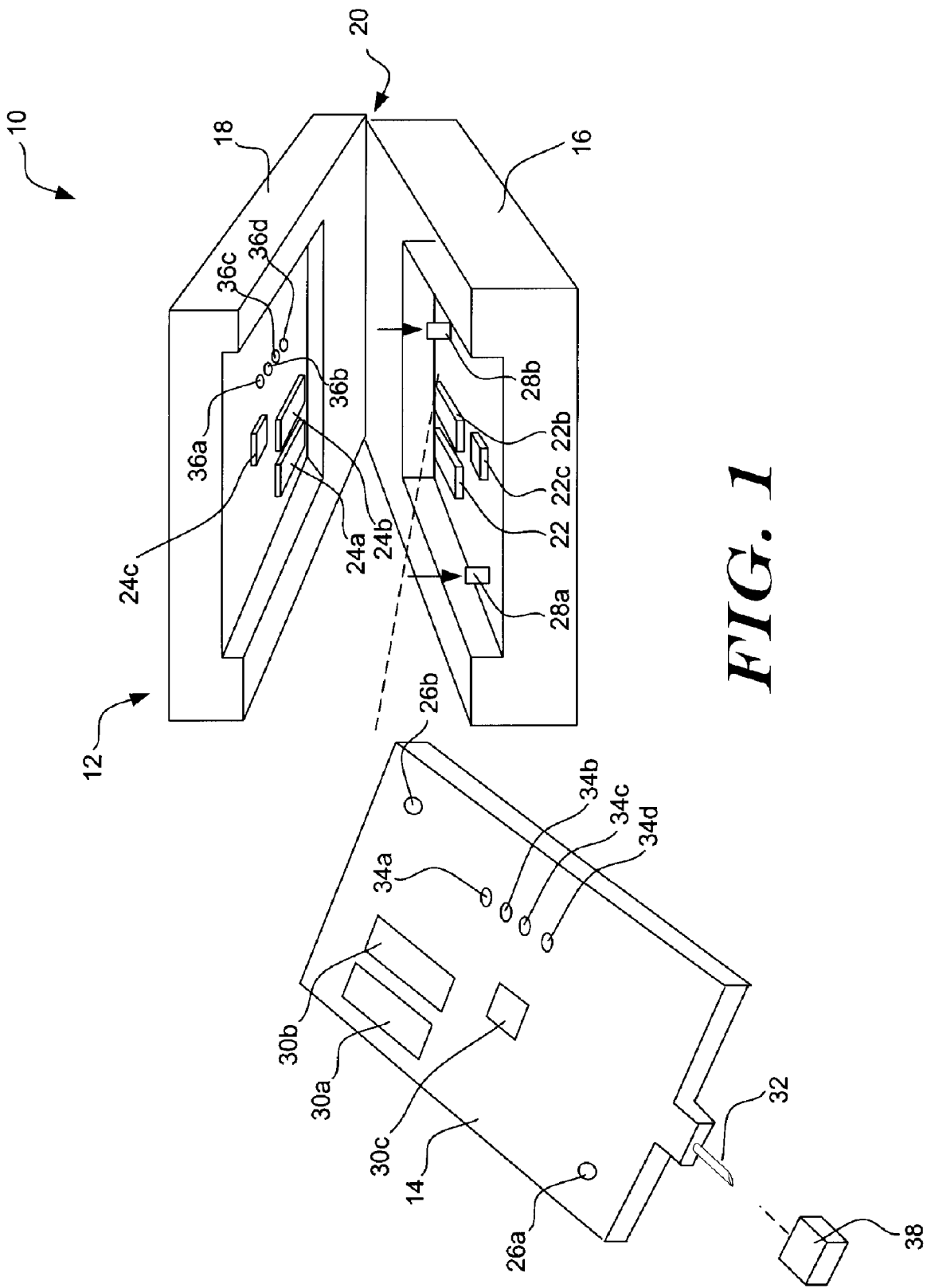
FIG. 1 is a perspective view of an illustrative sample analyzer and cartridge in accordance with the present invention.

FIG. 1 is a perspective view of an illustrative sample analyzer and cartridge in accordance with the present invention. The illustrative sample analyzer is generally shown at 10, and includes a housing 12 and a removable or disposable cartridge 14. The illustrative housing 12 includes a base 16, a cover 18, and a hinge 20 that attaches the base 16 to the cover 18, but this is not required. In the illustrative embodiment, the base 16 includes a first light source 22a, a second light source 22b, and a third light source 22c, along with associated optics and the necessary electronics for operation of the sample analyzer. Each of the light sources may be a single light source or multiple light sources, depending on the application. In some cases, the overall dimensions of the housing may be less than 1 cubic foot, less than one-half cubic foot, less than one-quarter cubic foot, or smaller, as desired. Likewise, the overall weight of the housing may be less than 10 pounds, less than 5 pounds, less than one pound, or less, as desired.

The illustrative cover 12 includes a pressure source (e.g. pressure-chambers with control microvalves), a first light detector 24a, a second light detector 22b, and a third light detector 22c, each with associated optics and electronics. Each of the light detectors may also be a single light detector or multiple light detectors, depending on the application. Polarizers and/or filters may also be provided, if desired, depending on the application.

The illustrative removable cartridge 14 is adapted to receive a sample fluid via a sample collector port, which in the illustrative embodiment, includes a lancet 32. The lancet 32 may be retractable and/or spring loaded, in some embodiments. A cap 38 may be used to protect the sample collector port and/or lancet 32 when the removable cartridge 14 is not in use.

In the illustrative embodiment, the removable cartridge 14 performs a blood analysis on a whole blood sample. The lancet 32 may be used to prick the finger of the user to produce a sample of blood, which through capillary action, may be drawn into an anti-coagulant coated capillary in the removable cartridge 14. The removable cartridge 14 may be constructed similar to the fluidic circuits available from Micronics Technologies, some of which are fabricated using a laminated structure with etched channels. However, it is contemplated that the removable cartridge 14 may be constructed in any suitable manner including by injection molding or any other suitable manufacturing process or method, as desired.

During use, and after a blood sample has been drawn into the removable cartridge 14, the removable cartridge 14 may be inserted into the housing when the cover 18 is in the open position. In some cases, the removable cartridge 14 may include holes 26a and 26b for receiving registration pins 28a and 28b in the base 16, which may help provide alignment and coupling between the different parts of the instrument. The removable cartridge 14 may also include a first transparent flow stream window 30a, a second transparent flow stream window 30b and a third transparent window 30c, which are in alignment with the first, second and third light sources 22a, 22b and 22c, and the first, second and third light detectors 24a, 24b and 24c, respectively.

When the cover is moved to the closed position, and the system is pressurized, the cover 18 may provide controlled pressures via pressure providing ports 36a, 36b, 36c, and 36d to pressure receiving ports 34a, 34b, 34c and 34c, respectively, in the illustrative removable cartridge 14. It is contemplated that more or less pressure providing and pressure receiving ports may be used, depending on the application. Alternatively, or in addition, it is contemplated that one or more micro-pumps, such as electrostatically actuated meso pumps, may be provided on or in the removable cartridge 14 to provide the necessary pressures to operate the fluidic circuit on the removable cartridge 14. Some illustrative electrostatically actuated meso pumps are described in, for example, U.S. Pat. Nos. 5,836,750, 6,106,245, 6,179,586, 6,729,856, and 6,767,190, all assigned to the assignee of the present invention, and all incorporated herein by reference.

Once pressurized, the illustrative instrument may perform a blood analysis on the collected blood sample. In some cases, the blood analysis may include a complete blood count (CBC) analysis, but other types of analysis can be performed, depending on the application.

To count and classify red blood cells, a portion of the whole blood sample may be partitioned and provided to a red blood measurement channel in the removable cartridge 14. The blood sample may then be diluted if desired, the red blood cells may be sphered on the fly, the resulting sample may be hydrodynamically focused for core formation and ultimately provided to a first cytometry channel. The first cytometry channel may be located along the first transparent flow stream window 30a of the removable cartridge 14 so that the cells in the flow stream can be optically interrogated by the first light source 22a and the first light detector 24a. In some cases, a first flow sensor may be provided on the removable cartridge 14 to provide a measure of the flow rate through the first cytometry channel.

In some cases, the measured parameters may include, for example, sample flow rate (FR), measurement time (T) duration, sample dilution factor (DF), number of red blood cells counted ($N_{RB}$), number of platelets counted ($N_{Plt}$), the diameter of each cell (drbc) and hemoglobin concentration of each cell (CHC). From these parameters, a number of red blood cell analysis parameters may be calculated including, for example, a red blood cell count (RBC=$N_{RB}$/(DF×FR×T)), a platelet count (Plt=$N_{Plt}$/(DF×FR×T)), a mean cell hemoglobin concentration (MCHC=<CHC>), a mean cell volume (MCV=($\pi$/6)×<drbc$^3$>), a mean cell hemoglobin content (MCH=($\pi$/6)×<drbc$^3$×CHC>), a relative distribution width (RDW=Standard Deviation of [($\pi$/6)×drbc$^3$]/MCV), a Hematocrit parameter (Hct=RBC×MCV) and/or a hemoglobin concentration (Hb=MCHC×Hct).

In some embodiments, some of the blood sample is also directed to an absorption measurement channel. The absorption measurement channel may be located along the third transparent window 30c of the removable cartridge 14 so that the blood sample can be optically interrogated by the third light source 22c and the third light detector 24c. A flow sensor may be provided on the removable cartridge 14 to provide a measure of the flow rate into or through the absorption measurement channel. The absorption measurement channel may provide a measure of the absorption of the incident light provided by the third light source 22c. The measured absorption level may provide an indication of the bulk or mean cell hemoglobin concentration in the blood sample.

To count and classify white blood cells, a portion of the whole blood sample may be partitioned and provided to a white blood measurement channel in the removable cartridge 14. The blood sample may then be diluted if desired, the red blood cells may be lysed on the fly, the resulting sample may be hydrodynamically focused for core formation and ultimately provided to a second cytometry channel. The second cytometry channel may be located along the second transparent flow stream window 30b of the removable cartridge 14 so that the cells in the flow stream can be optically interrogated by the second light source 22b and the second light detector 24b. A flow sensor may be provided on the removable cartridge 14 to provide a measure of the flow rate through the second cytometry channel. In some cases, measured white blood cell parameters may include, for example, three (3) or (5) part white cell differentiation, total white blood cell count and/or on-axis white blood cell volume. Other parameters may also be measured or calculated, depending on the application.

FIG. 1 shows one illustrative sample analyzer and cartridge assembly. However, it is contemplated that other sample analyzer configurations may be used. For example, the sample analyzer 10 and removable cartridge may be similar to that described in U.S. Patent Application 2004/0211077 to Schwichtenberg et al., which is incorporated herein by reference.

In some cases, the sample analyzer 10 is adapted to be used at the point of care of a patient such as in a doctor's office, in the home, or elsewhere in the field. The ability to provide a sample analyzer 10 that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis.

During operation, the sample analyzer 10 may receive a collected sample, such as a collected whole blood sample, and once the analyzer is activated, the sample analyzer 10 may automatically process the sample and provide information to the user to make a clinical decision. In some embodiments, the sample analyzer 10 may display or print out quantitative results (e.g. inside and/or outside of a predefined range), such that no further calculations or interpretation is required by the user.

Figure 2:
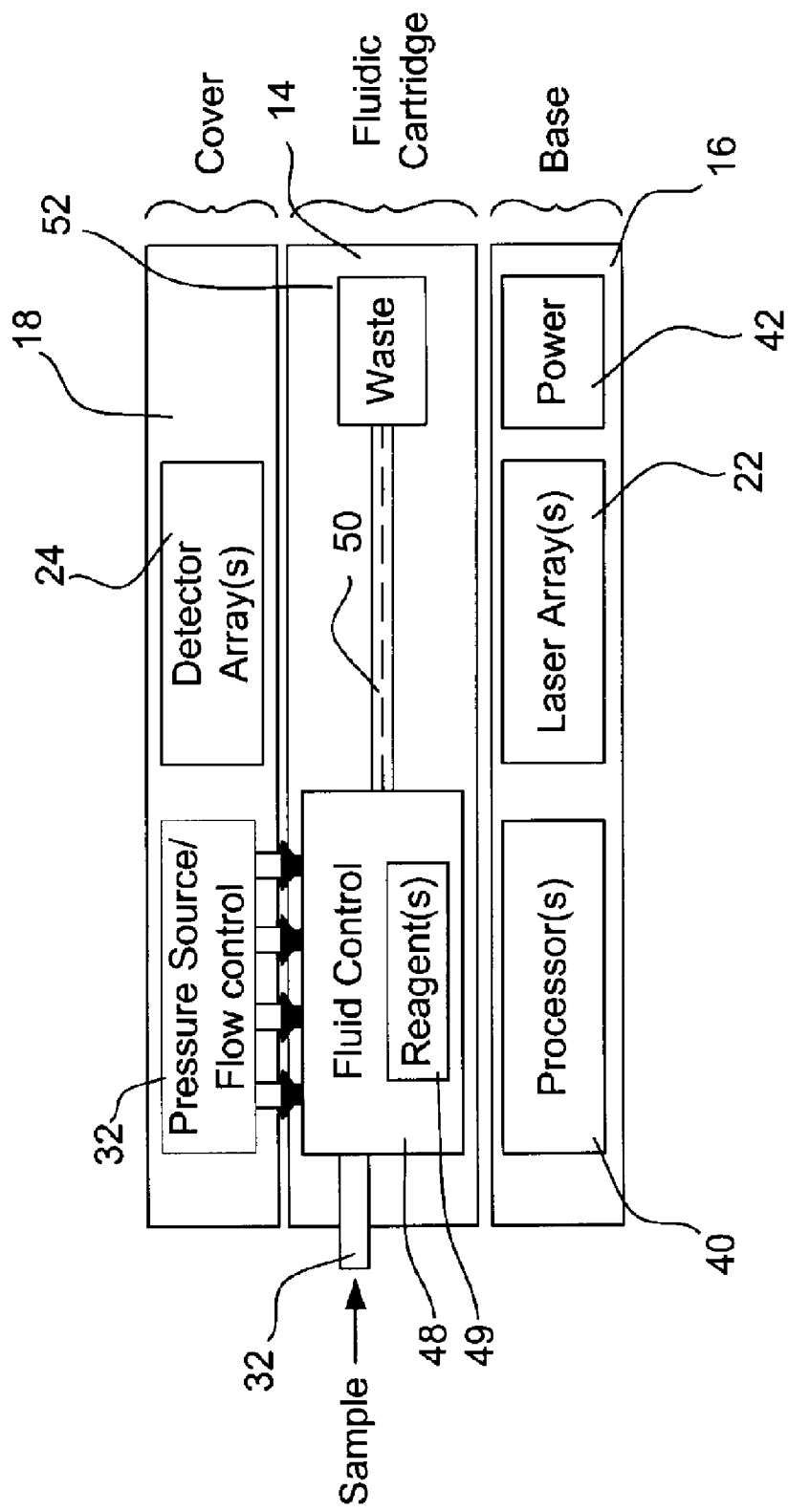
FIG. 2 is a schematic view of the illustrative sample analyzer and cartridge of FIG. 1.

FIG. 2 is a schematic view of the illustrative sample analyzer and cartridge of FIG. 1. As detailed above, and in the illustrative embodiment, the base 16 may include a number of light sources 22, associated optics and the necessary control and processing electronics 40 for operation of the analyzer. The base 16 may also include a battery 42, transformer or other power source. The cover 12 is shown having a pressure source/flow control block 44 and a number of light detectors 24 with associated optics.

The removable cartridge 14 may receive a sample fluid via the sample collector port or lancet 32. When pressurized by the pressure source/flow control block 44, the removable cartridge 14 may perform a blood analysis on the received blood sample. In some embodiments, and as described above, the removable cartridge 14 may include a number or reagents 49, and a fluidic circuit for mixing the reagents with the blood sample to prepare the blood sample for analysis. Also, the removable cartridge 14 may include a number of flow sensors to help control and/or verify the proper operation of the fluidic circuit.

In some cases, the blood sample is prepared (e.g. lysed, sphered, stained, diluted and/or otherwise processed) and then hydrodynamically focused for core formation in one or more on-board cytometry channels, such as cytometry channel 50. In the illustrative embodiment, the cytometry channel 50 is routed past a transparent flow stream window such as the first transparent flow stream window 30a in the removable cartridge 14. An array of light sources 22 and associated optics in the base 16 may provide light through the core stream via the flow stream window 30a. An array of light detectors 24 and associated optics may receive scattered and non-scattered light from the core, also via the flow stream window 30a. The controller or processor 40 may receive output signals from the array of detectors 24, and may differentiate and/or counts selected cells that are present in the core stream.

It is contemplated that the removable cartridge 14 may include a fluid control block 48 for helping to control the velocity of at least some of the fluids on the removable cartridge 14. In the illustrative embodiment, the fluid control block 48 may include flow sensors for sensing the velocity of the various fluids and report the velocities to the controller or processor 40. The controller or processor 40 may then adjust one or more control signals, which are provided to the pressure source/flow control block 44, to achieve the desired pressures and thus the desired fluid velocities for proper operation of the analyzer.

Because blood and other biological waste can spread disease, the removable cartridge 14 may include a waste reservoir 52 downstream of the illustrative cytometry channel 50. The waste reservoir 52 may receive and store the fluid of the flow stream in the removable cartridge 14. When a test is completed, the removable cartridge 14 may be removed from the analyzer and disposed of, preferably in a container compatible with biological waste.

Figure 3:
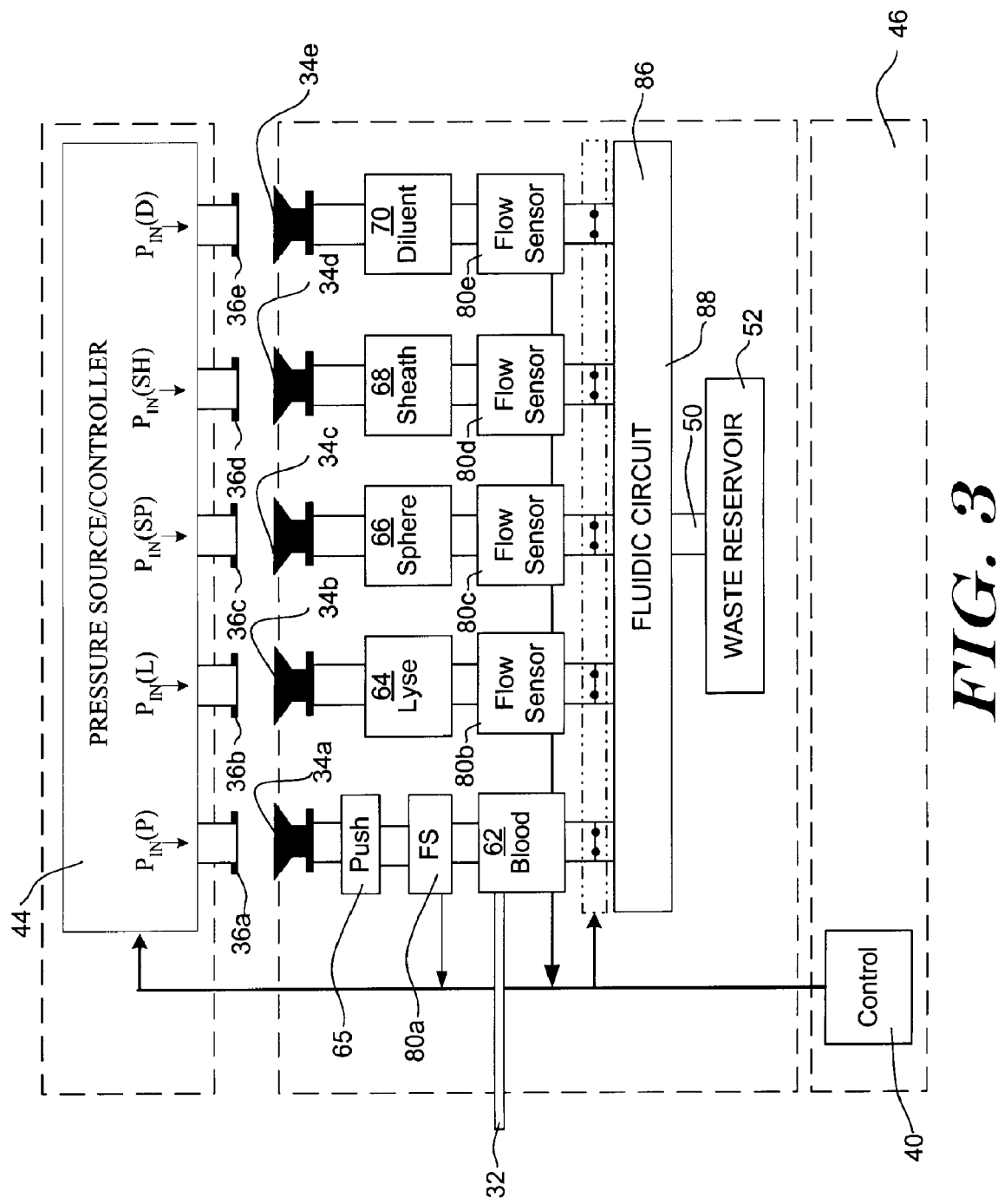
FIG. 3 is a more detailed schematic diagram showing the flow control of the sample analyzer and cartridge of FIG. 2.

FIG. 3 is a more detailed schematic diagram showing the flow control of the sample analyzer and cartridge of FIG. 2. In the illustrative embodiment, the pressure source/flow controller 44 in the cover 18 provides five controlled pressures including a Sample Push (P) pressure 36a, a lyse (L) pressure 36b, a sphere (SP) pressure 36c, a sheath (SH) pressure 36d, and a diluent (D) pressure 36e. These are only illustrative, and it is contemplated that more, less or different pressures (e.g. stain pressure to a stain reservoir) may be provided by pressure source/flow controller 44, depending on the application. Also, it is contemplated that the cover 18 may not include a pressure source/flow controller 44 at all. Instead, the removable cartridge 14 may include an on-board pressure source, such as a compressed air reservoir, one or more micro-pumps such as electrostatically actuated meso pumps as described above, or any other suitable pressure source, as desired. The array of light sources and detectors are not shown in FIG. 3.

In the illustrative embodiment, pressure source 36a provides pressure to a blood sample reservoir 62 via a pusher fluid 65, pressure source 36b provides pressure to a lyse reservoir 64, pressure source 36c provides pressure to a sphere reservoir 66, pressure source 36d provides pressure to a sheath reservoir 68, and pressure source 36e provides pressure to a diluent reservoir 70.

In one illustrative embodiment, each pressure source may include a first pressure chamber for receiving an input pressure, and a second pressure chamber for providing a controlled pressure to the removable cartridge. A first valve may be provided between the first pressure chamber and the second pressure chamber for controllably releasing the pressure in the first pressure chamber to the second pressure chamber. A second valve, in fluid communication with the second pressure chamber, may controllably vent the pressure in the second pressure chamber to atmosphere. This may allow the pressure source/flow controller 44 to provide a controlled pressure to each of the pressure receiving ports on the removable cartridge 14. Each valve may be an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Alternatively, each valve may be an array of electrostatically actuated microvalves that are pulse modulated with a controllable duty cycle to achieve a controlled "effective" flow or leak rate. Other valves may also be used, if desired.

The illustrative removable cartridge 14 includes five pressure receiving ports 34a, 34b, 34c, 34d and 34e, each for receiving a corresponding controlled pressure from the pressure source/flow controller 44. In the illustrative embodiment, the pressure receiving ports 34a, 34b, 34c, 34d and 34e direct the controlled pressures to the blood reservoir 62, the lyse reservoir 64, the sphere reservoir 66, the sheath reservoir 68, and the diluent reservoir 70, respectively. The lyse reservoir 64, sphere reservoir 66, sheath reservoir 68 and diluent reservoir 70 may be filled before the removable cartridge 14 is shipped for use, while the blood reservoir 62 may be filled in the field via sample collector port or lancet 32.

As shown, a flow sensor may be provided in-line with each or selected fluids. Each flow sensor 80a-80e may measure the velocity of the corresponding fluid. The flow sensors 80a-80e are preferably thermal anemometer type flow sensors, and more preferably microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor 80a-80e may be provided to controller or processor 40. The controller or processor 40 may provide control signals to the pressure source/controller 44, as shown. For example, to control the pressure provided to the blood sample, the controller or processor 40 may open a first valve between a first pressure chamber and a second pressure chamber in the pressure source/controller 44 for controllably releasing a pressure in the first pressure chamber to the second pressure chamber when the velocity of the blood sample drops below a first predetermined value. Likewise, the controller or processor 40 may open a second valve that vent the pressure in the second pressure chamber when the velocity of the blood sample increases above a second predetermined value. The controller or processor 40 may control the velocities of the lysing reagent, sphering reagent, sheath fluid and diluent in a similar manner.

In some cases, the controller or processor 40 may detect one or more changes in the flow rate passing through a flow channel. A change in flow rate may correspond to, for example, one or more bubbles in a flow channel, an occlusion or partial occlusion of a flow channel caused by, for example, coagulation of the blood sample, unwanted or foreign objects in a flow channel, and/or other undesirable characteristics of a flow channel. The controller or processor 40 may be programmed to detect such characteristics from the flow rate, and in some cases, issue a warning and/or shut down the sample analyzer.

Thermal anemometer type flow sensors typically include a heater element that, when energized, produces one or more heat pulses in the fluid, and further includes one or more heat sensors positioned upstream and/or downstream of the heater element to detect the one or more heat pulses. The velocity of the fluid through the flow channel may be related to the time that it takes for a heat pulse to travel from the heater element to one of the spaced heat sensors.

In some cases, thermal anemometer type flow sensors may be used to detect the thermal conductivity and/or specific heat of the fluid. Changes in the thermal conductivity and/or specific heat of the fluid may correspond to changes in the fluid characteristics, such as a change of state of the fluid (coagulation of a blood sample), bubbles in the fluid, unwanted or foreign objects in the fluid, etc. Thus, and in some embodiments, it is contemplated that the controller or processor 40 may detect characteristics of the fluid by monitoring the thermal conductivity and/or specific heat of the fluid that passes by the thermal anemometer type flow sensors.

In some cases, an impedance sensor may be provided in fluid communication with a flow channel. The controller or processor 40 may be coupled to the impedance sensor. Changes in the impedance of the fluid may indicate a change in fluid characteristics, such as a change in the state of the fluid (coagulation of a blood sample), bubbles in the fluid, unwanted or foreign objects in the fluid, etc. Thus, and in some embodiments, it is contemplated that the controller or processor 40 may detect characteristics of the fluid by monitoring the impedance of the fluid that passes by the impedance sensor.

Downstream valves generally shown at 110 may also be provided. Controller or processor 40 may open/close downstream valves 110, as desired. For example, the downstream valves 110 may remain closed until the system is fully pressurized. This may help prevent the blood, lysing reagent, sphering reagent, sheath fluid and diluent from flowing into the fluidic circuit 86 before the system is fully pressurized. Also, the downstream valves 110 may be controlled to aid in performing certain tests, like zero-flow tests, etc. In another embodiment, downstream valves 110 may be opened by mechanical action when, for example, the cover is closed.

Figure 4:
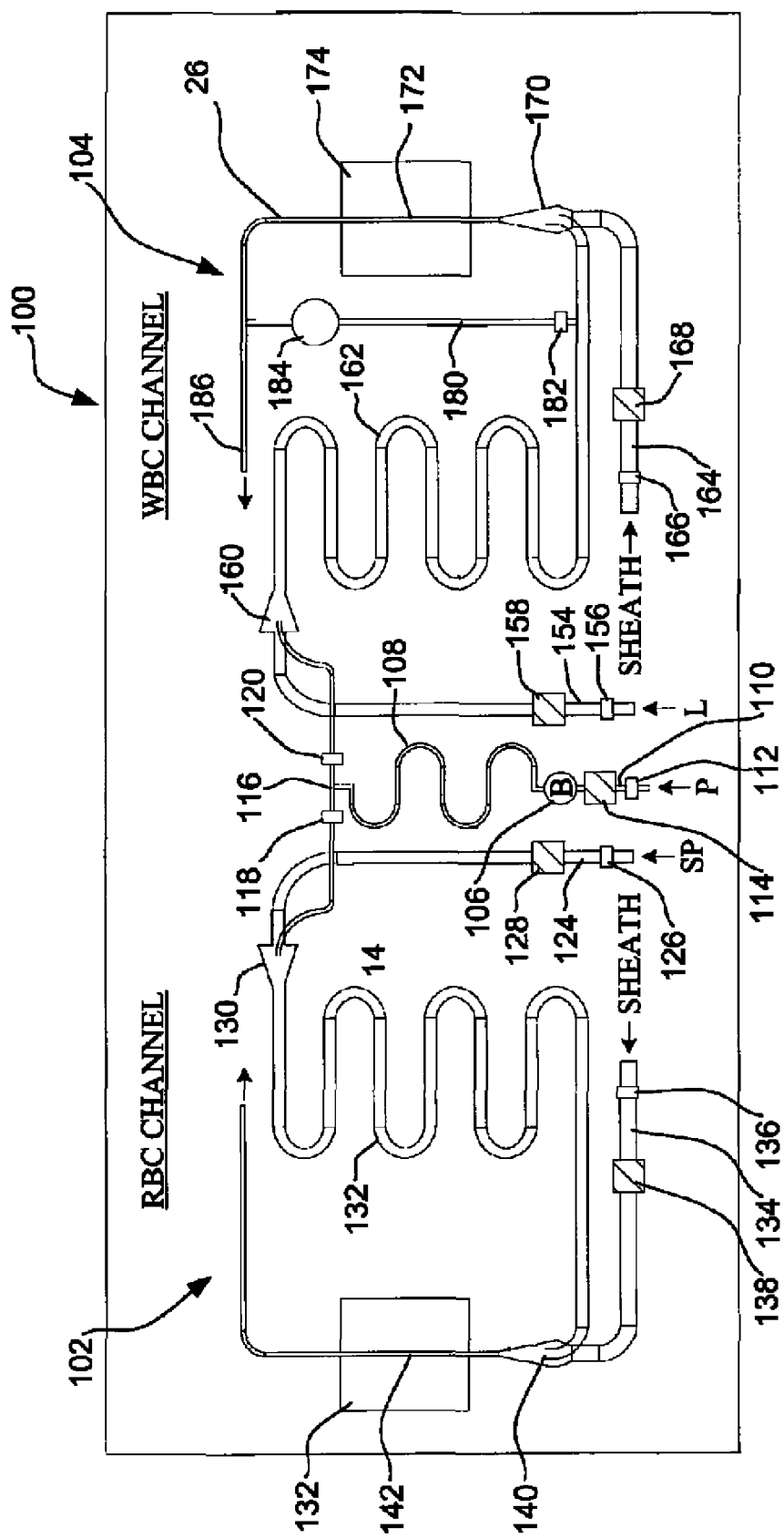
FIG. 4 is a schematic view of certain features of an illustrative cartridge in accordance with the present invention.

FIG. 4 is a schematic view of certain features of an illustrative removable cartridge in accordance with the present invention. The illustrative removable cartridge is generally shown at 100, and may be similar to removable cartridge 14 shown and described above with reference to FIGS. 1-3. It should be understood that the removable cartridge 100 is only illustrative, and that the present invention can be applied to many microfluidic cartridges, regardless of form, function or configuration. For example, the present invention may be applied to removable cartridges adapted for flow cytometry, hematology, clinical chemistry, blood chemistry analysis, urinalysis, blood gas analysis, virus analysis, bacteria analysis, electrolyte measurements, etc. It is also contemplated that the removable cartridges of the present invention, such as removable cartridge 100, may be made from any suitable material or material system including, for example, glass, silicon, one or more polymers, or any other suitable material or material system, or combination of materials or material systems.

The illustrative removable cartridge 100 includes a first measurement channel 102 and a second measurement channel 104, although more or less measurement channels may be used, as desired. The first measurement channel 102, in the illustrative embodiment, is a red blood cell measurement channel, and the second measurement channel 104 is a white blood cell measurement channel. A whole blood sample is received by the removable cartridge 100 via blood receiving port 106, which through capillary action, draws in a known amount of blood into an anti-coagulant coated blood sample storage capillary 108. A Sample Push (P) pressure, such as a Sample Push (P) pressure 36a of FIG. 3, is provided to a sample push fluid reservoir, such as Sample Push Fluid Reservoir 65 of FIG. 3. When pressure is applied, the sample push fluid is forced from the sample push fluid reservoir into a blood sample push channel 110.

In some illustrative embodiments, a valve 112 and a flow sensor 114 may be provided in line with the blood sample push channel 110. The valve 112 may be controlled to open when it is desirable to push the blood sample through the fluidic circuit. The flow sensor 114 may measure the flow rate of the blood sample push fluid, and thus the blood sample flow rate through the anti-coagulant coated capillary 108. The flow rate provided by the flow sensor 114 may be used to help control the Sample Push (P) pressure that is provided to the removable cartridge 100.

In the illustrative embodiment, the whole blood sample is partitioned and provided to the red blood cell measurement channel 102 and the white blood cell measurement channel 104 via branch 116. In the illustrative embodiment, a valve 118 is provided in line with the branch to control the blood sample flow into the red blood cell measurement channel 102, and a valve 120 is provided to control the blood sample flow into the white blood cell measurement channel 104.

Turning specifically to the red blood cell measurement channel 102, a red blood cell sphering reagent pressure (SP), such as a Sphering Pressure (SP) 36c of FIG. 3, is provided to a sphering reagent reservoir, such as Sphering Reservoir 66 of FIG. 3. When pressure is applied, the sphering reagent in the Sphering Reservoir 66 is forced into a sphering reagent channel 124.

In some illustrative embodiments, a valve 126 and a flow sensor 128 may also be provided in line with the sphering reagent channel 124. The valve 126 may be controlled to open when it is desirable to push the sphering reagent into the fluidic circuit. The flow sensor 128 may measure the flow rate of the sphering reagent, and provide a measure of the sphering reagent flow rate through the sphering reagent channel 124. The flow rate provided by the flow sensor 128 may be used to help control the Sphering Pressure (SP) that is provided to the removable cartridge 100 by the pressure source/controller 44.

During normal functional operation of the illustrative removable cartridge 100, the sphering reagent is pushed into an intersecting region 130 at a sphering reagent flow rate, and the blood sample is pushed into the intersecting region 130 at a blood sample flow rate. The blood sample flow rate and the sphering reagent flow rate may be controlled by the pressure source/controller 44 of FIG. 3.

The intersection region 130 may be configured so that the sphering reagent flows circumferentially around the blood sample when both fluids are flowing through the intersection region 130. In some cases, the sphering reagent flow rate may be higher than the blood sample flow rate, which may help improve the flow characteristics in a downstream sphering-on-the-fly channel 132, and in some cases, to help form a thin ribbon of blood that is completely and uniformly surrounded by the sphering reagent. Such a ribbon flow may help the sphering reagent uniformly sphere the red blood cells as they travel through the sphering-on-the-fly channel 132. Furthermore, the length of the sphering-on-the-fly channel 132, in conjunction with the flow rate of the sphering reagent and blood sample, may be set such that the blood sample is exposed to the sphering reagent for an appropriate amount of time.

A Sheath Fluid (SH) pressure, such as a Sheath (SH) pressure 36d of FIG. 3, may be provided to a sheath fluid reservoir, such as Sheath Fluid Reservoir 68 of FIG. 3. When pressure is applied, the sheath fluid is forced from the Sheath Fluid Reservoir 68 into a sheath channel 134. In some illustrative embodiments, a valve 136 and a flow sensor 138 may be provided in line with a sheath channel 134. The valve 136 may be controlled to open when it is desirable to push the sheath fluid into the fluidic circuit. The flow sensor 138 may measure the flow rate of the sheath fluid, and may provide a measure of the sheath flow rate through the sheath channel 134. The flow rate provided by the flow sensor 138 may be used to help control the Sheath Pressure (SH) that is provided to the removable cartridge 100.

In the illustrative embodiment, the sheath fluid is provided to an intersecting region 140 at a sheath fluid flow rate, and the sphered blood sample is provided to the intersecting region 140 at a sphered blood sample flow rate. The sphered blood sample flow rate and the sheath flow rate may be controlled by a pressure source/controller, such as pressure source/controller 44 of FIG. 3.

The intersection region 140 may be configured so that the sheath fluid flows circumferentially around the sphered blood sample when both fluids are flowing through the intersection region 140. In some cases, the sheath flow rate is significantly higher than the sphered blood sample flow rate, which may help improve core formation in a downstream flow cytometry channel 142. For example, in some flow cytometry applications, the intersecting region 140 may be configured to hydrodynamically focus and arrange the sphered blood cells in a single file core so that each red blood cell can be individually optically interrogated by an analyzer as they pass through an optical window region 144 in the removable cartridge 100. In some cases, the fluid that passes through the cytometry channel 142 is directed to an on-board waste reservoir.

Turning now to the white blood cell measurement channel 104, a white blood cell lysing reagent pressure (L), such as a Lysing Pressure (L) 36b of FIG. 3, is provided to a lysing reagent reservoir, such as Lyse Reservoir 64 of FIG. 3. When pressure is applied, the lysing reagent in the Lyse Reservoir 64 is forced into a lysing reagent channel 154.

In some illustrative embodiments, a valve 156 and a flow sensor 158 may be provided in line with the lysing reagent channel 154. The valve 156 may be controlled to open when it is desirable to push the lysing reagent into the fluidic circuit. The flow sensor 158 may measure the flow rate of the lysing reagent, and provide a measure of the lysing reagent flow rate through the lysing reagent channel 154. The flow rate provided by the flow sensor 158 may be used to help control the Lysing Pressure (L) that is provided to the removable cartridge 100 by the pressure source/controller 44.

During normal functional operation of the illustrative removable cartridge 100, the lysing reagent is provided to an intersecting region 160 at a lysing reagent flow rate, and the blood sample is provided to the intersecting region 160 at a blood sample flow rate. The blood sample flow rate and the lysing reagent flow rate may be controlled by a pressure source/controller, such as pressure source/controller 44 of FIG. 3.

The intersection region 160 may be configured so that the lysing reagent flows circumferentially around the blood sample when both fluids are flowing through the intersection region 160. In some cases, the lysing reagent flow rate may be higher than the blood sample flow rate, which may help improve the flow characteristics in a lysing-on-the-fly channel 162, and in some cases, to help form a thin ribbon of blood that is completely and uniformly surrounded by the lysing reagent. Such a ribbon flow may help the lysing reagent uniformly lyse the red blood cells as they travel through the lysing-on-the-fly channel 162. Furthermore, the length of the lysing-on-the-fly channel 162, in conjunction with the flow rate of the lysing reagent and blood sample, may be set such that the blood sample is exposed to the lysing reagent for an appropriate amount of time.

A Sheath Fluid (SH) pressure, such as a Sheath (SH) pressure 36d of FIG. 3, may be provided to a sheath fluid reservoir, such as Sheath Fluid Reservoir 68 of FIG. 3. When pressure is applied, the sheath fluid is forced from the Sheath Fluid Reservoir 68 into a sheath channel 164. In some illustrative embodiments, a valve 166 and a flow sensor 168 may be provided in line with a sheath channel 164. The valve 166 may be controlled to open when it is desirable to push the sheath fluid into the fluidic circuit. The flow sensor 168 may measure the flow rate of the sheath fluid, and may provide a measure of the sheath flow rate through the sheath channel 164. The flow rate provided by the flow sensor 168 may be used to help control the Sheath Pressure (SH) that is provided to the removable cartridge 100. In some cases, the sheath flow rate through sheath channel 164 is the same as the sheath flow rate through sheath channel 134. However, in other cases, the sheath flow rate through sheath channel 164 may be different from the sheath flow rate through sheath channel 134.

In the illustrative embodiment, the sheath fluid is provided to an intersecting region 170 at a sheath fluid flow rate, and the lysed blood sample is provided to the intersecting region 170 at a lysed blood sample flow rate. The lysed blood sample flow rate and the sheath flow rate may be controlled by a pressure source/controller, such as pressure source/controller 44 of FIG. 3.

The intersection region 170 may be configured so that the sheath fluid flows circumferentially around the lysed blood sample when both fluids are flowing through the intersection region 170. In some cases, the sheath flow rate is significantly higher than the lysed blood sample flow rate, which may help improve core formation in a downstream flow cytometry channel 172. For example, in some flow cytometry applications, the intersecting region 170 may be configured to hydrodynamically focus and arrange the white blood cells in the lysed blood sample in a single file core so that each white blood cell can be individually optically interrogated by an analyzer as they pass through an optical window region 174 in the removable cartridge 100. In some cases, the fluid that passes through the cytometry channel 172 is provided to an on-board waste reservoir.

Figure 8:
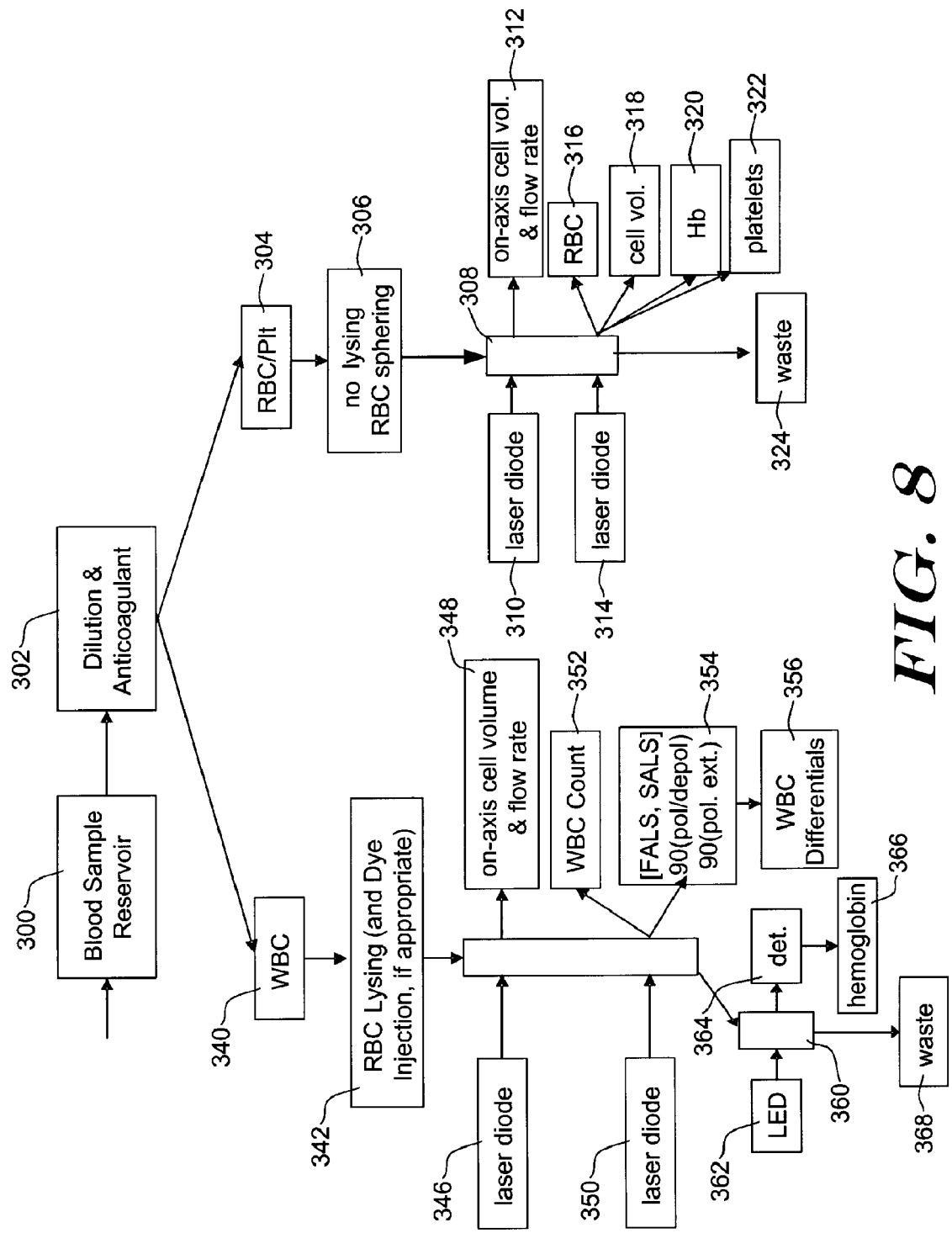
FIG. 8 is a schematic flow diagram showing another illustrative method for analyzing a blood sample in accordance with the present invention.

In some cases, an absorption measurement channel may also be provided. In the illustrative embodiment, a portion of the lysed blood sample is provided to absorption channel 180. A valve 182 may be provided to selectively allow a portion of the lysed blood sample to pass to the absorption channel or region 184. The analyzer may include a light source to illuminate the absorption channel or region 184, as well as a detector to detect the light that is not absorbed by the lysed blood sample in the absorption channel or region 184. The analyzer may then determine an absorption level, from which a bulk absorption based hemoglobin measurement can be made. In some cases, and as shown in FIG. 8, the absorption channel 184 may be situated downstream of the cytometry channel 172, if desired. In other cases, a whole blood sample may be provided directly, such as from branch 116, to an absorption channel. In such cases, the absorption channel may include a mechanism to lyse the red blood cells prior to taking the absorption measurement. While the illustrative removable cartridge 100 is adapted to perform a Complete Blood Count (CBC) analysis on a whole blood sample, it is contemplated that other removable cartridge configurations and analysis types may be used, as desired.

Figure 5:
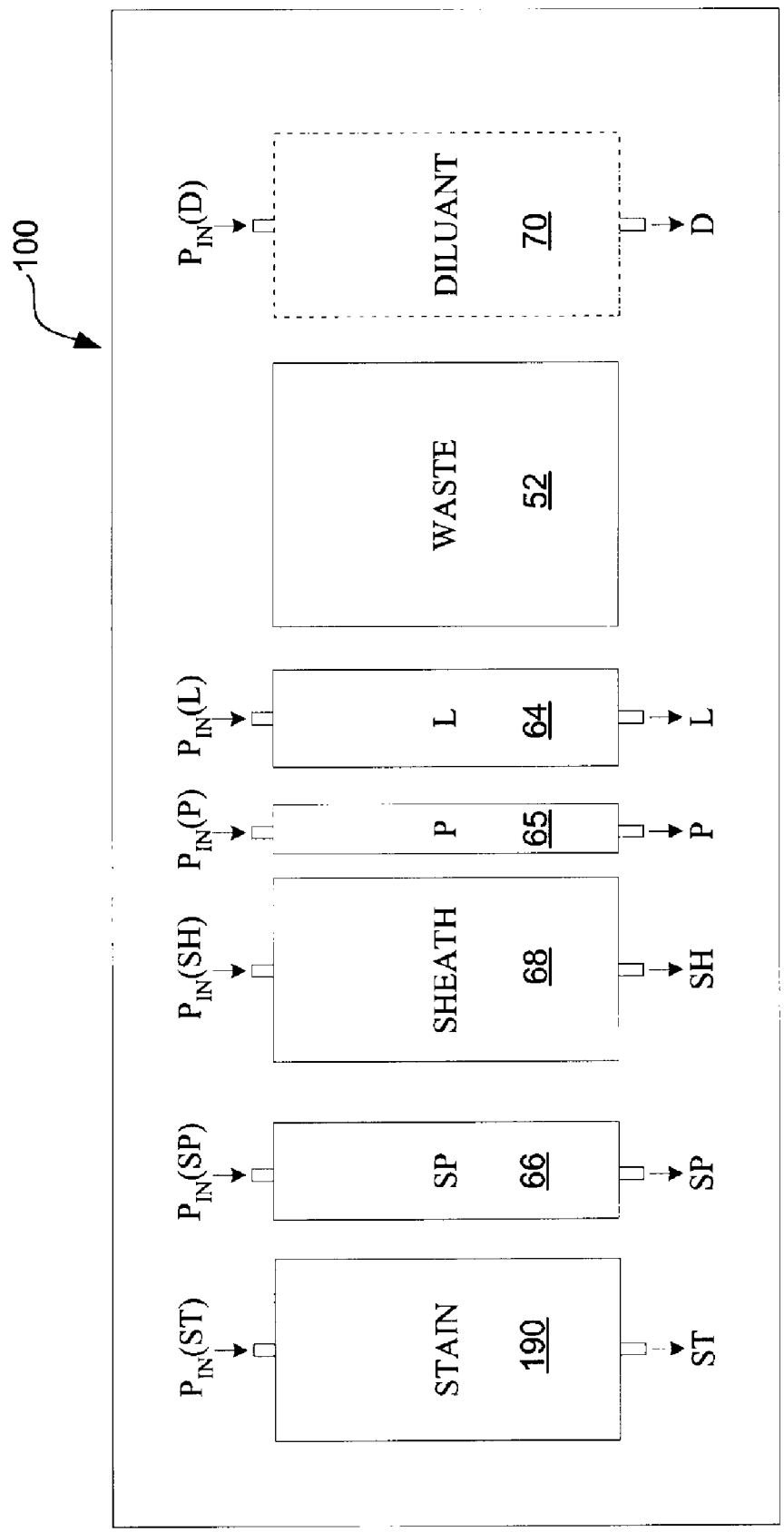
FIG. 5 is a schematic view of a number of illustrative storage reservoirs that can be included in a cartridge in accordance with the present invention.

FIG. 5 is a schematic view of a number of illustrative storage reservoirs that can be included in a removable cartridge in accordance with the present invention. In the illustrative embodiment, a removable cartridge such as removable cartridge 100 of FIG. 4 may include, for example, a lysing reagent reservoir 64, a pusher fluid reservoir 65, a sphering reagent reservoir 66, a sheath fluid reservoir 68, a diluent fluid reservoir 70, a stain reservoir 190 and a waste reservoir 52. These are only illustrative, and it is contemplated that more, less or different reservoirs may be provided on or in a removable cartridge.

Each reservoir may be sized and include an appropriate amount of fluid and/or reagent to support the desired operation of the removable cartridge. The diluent reservoir 70 may include a diluent fluid for diluting the incoming sample, such as a whole blood sample. In the illustrative embodiment of FIG. 4, the sphering reagent and/or lysing reagents may perform the function of a diluent, and therefore, a separate diluent reservoir 70 may not be required or even desired. Likewise, and in some embodiments, a stain reservoir such as stain reservoir 190 may be desirable to add a stain to the white blood cell channel to support white blood cell differentiation. It is contemplated that the reagents and/or fluids stored in the reservoirs may initially be in liquid or lyophilized form, depending on the application.

Figure 6:
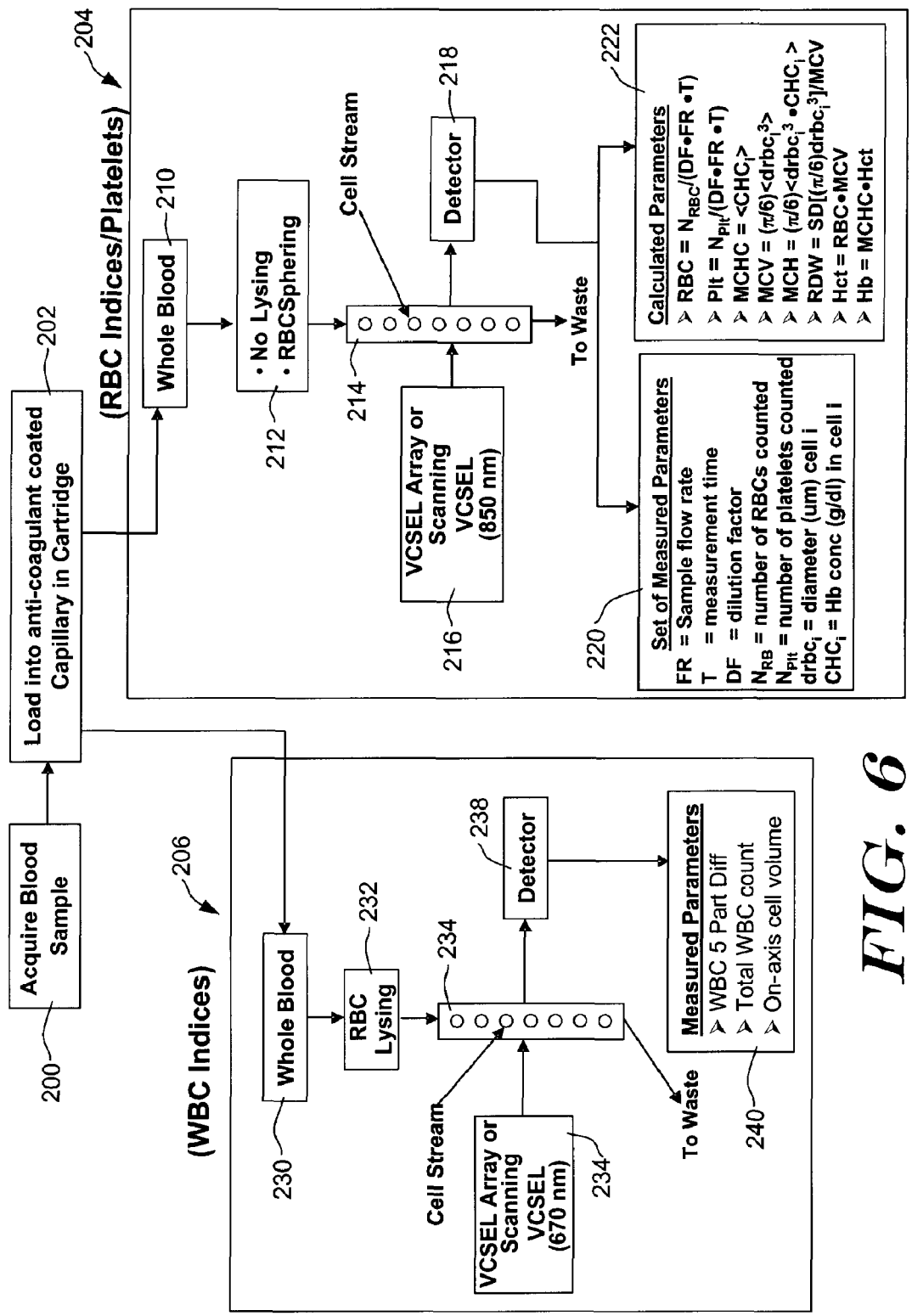
FIG. 6 is a schematic flow diagram showing an illustrative method for analyzing a blood sample in accordance with the present invention.

FIG. 6 is a schematic flow diagram showing an illustrative method for analyzing a blood sample using a removable cartridge in accordance with the present invention. In the illustrative method, a blood sample is first acquired at step 200. Next, the blood sample is provided to an anti-coagulant coated capillary in a removable cartridge. The blood sample is then partitioned and provided to a Red Blood Cell and Platelet (RBC/P) measurement channel 204 and a White Blood Cell (WBC) measurement channel 206.

In the RBC/P measurement channel 204, the red blood cells are first sphered as shown at 212, and then hydrodynamically focused and provided single file down a RBC/P cytometry channel 214 in the removable cartridge. A light source 216, such as a Vertical Cavity Surface Emitting Laser (VCSEL), shines light on the individual cells as they pass by an analysis region of the RBC/P cytometry channel 214. In some cases, an array of VCSEL devices is provided, and only the VCSEL(s) that is/are aligned with the individual cells as they pass by the analysis region of the RBC/P cytometry channel 214 is activated. Some of the incident light provided by the VCSEL is scattered, and a detector 218 detects the scattered light. In some cases, the detector 218 detects both Forward Angle Scatter Light (FALS) and Small Angle Scatter Light (SALS).

In some cases, a laser (or other) source is focused into the RBC/P cytometer channel 214, either as an elongated line source or as two separate spot sources. The RBC and Platelets in the RBC/P cytometer channel 214 through the focused light. High quality collection optics may be used to form a sharp image of the cells and focused illumination onto an opaque screen containing one, two or more parallel slits whose longitudinal axes are preferably arranged orthogonal to the flow direction in the RBC/P cytometer channel 214. The distance between the slits may be, for example, on the order of the mean cell separation expected in the RBC/P cytometer channel 214. The opaque screen containing the slits may be placed in front of one or more detectors 218. As the image of a cell passes over a slit, it obscures the light incident on the slit and causes a reduction in the signal on the detector 218, producing a pulse waveform whose width is proportional to the cell diameter. When two spaced slits are provided, the two waveforms may permit the calculation of the cell flow velocity, and hence the cell size. High signal-to-noise may be obtained using this technique, which permits easy counting of events and identification of multiple cell events. Pulse width and amplitude may further enable the discrimination of some cell types.

In some cases, an image of both the cell and the light source is imaged on a double slit aperture placed in front of the detector 218. The double slit aperture provides a well defined geometrical aperture and high signal-to-noise ratio to count cells. As discussed above, signals from the slits may permit the accurate measurement of cell flow velocity, which in turn may permit the calculation of cell diameter.

In some cases, and as shown at 220, a number of parameters may be measured during this analysis, including for example, sample flow rate (FR), measurement time (T) duration, and sample dilution factor (DF). By monitoring the output of the detector(s), and/or the corresponding scatter signature, the number of red blood cells ($N_{RB}$), the number of platelets ($N_{Plt}$), the diameter of each cell (drbc) and the hemoglobin concentration of each cell may be measured.

From these parameters, and as shown at 282, a number of red blood cell analysis parameters may be calculated including, for example, a red blood cell count (RBC=$N_{RB}$/(DF×FR× T)), a platelet count (Plt=$N_{Plt}$/(DF×FR×T)), a mean cell hemoglobin concentration (MCHC=<CHC>), a mean cell volume (MCV=($\pi$/6)×<drbc$^3$>), a mean cell hemoglobin content (MCH=($\pi$/6)×<drbc$^3$×CHC>), a relative distribution width (RDW=Standard Deviation of [($\pi$/6)×drbc$^3$]/MCV), a Hematocrit parameter (Hct=RBC×MCV) and/or a hemoglobin concentration (Hb=MCHC×Hct).

In the illustrative WBC measurement channel 206, the red blood cells are first lysed as shown at 232, and then hydrodynamically focused and provided single file down a WBC cytometry channel 234 in the removable cartridge. A light source 236, such as a Vertical Cavity Surface Emitting Laser (VCSEL), shines light on the individual cells as they pass by an analysis region of the WBC cytometry channel 234. In some cases, an array of VCSEL devices is provided, and only the VCSEL(s) that is/are aligned with the individual cells as they pass by the analysis region of the WBC cytometry channel 234 is activated. Some of the incident light provided by the VCSEL is scattered, and a detector 238 detects the scattered light. In some cases, the detector 238 detects Forward Angle Scatter Light (FALS), Small Angle Scatter Light (SALS), and Large Angle Scatter Light (LASL). In some cases, and as shown at 240, a number of parameters may be measured during the analysis including, for example, on-axis cell volume, total WBC count, and WBC five (5) part differentiation.

Figure 7:
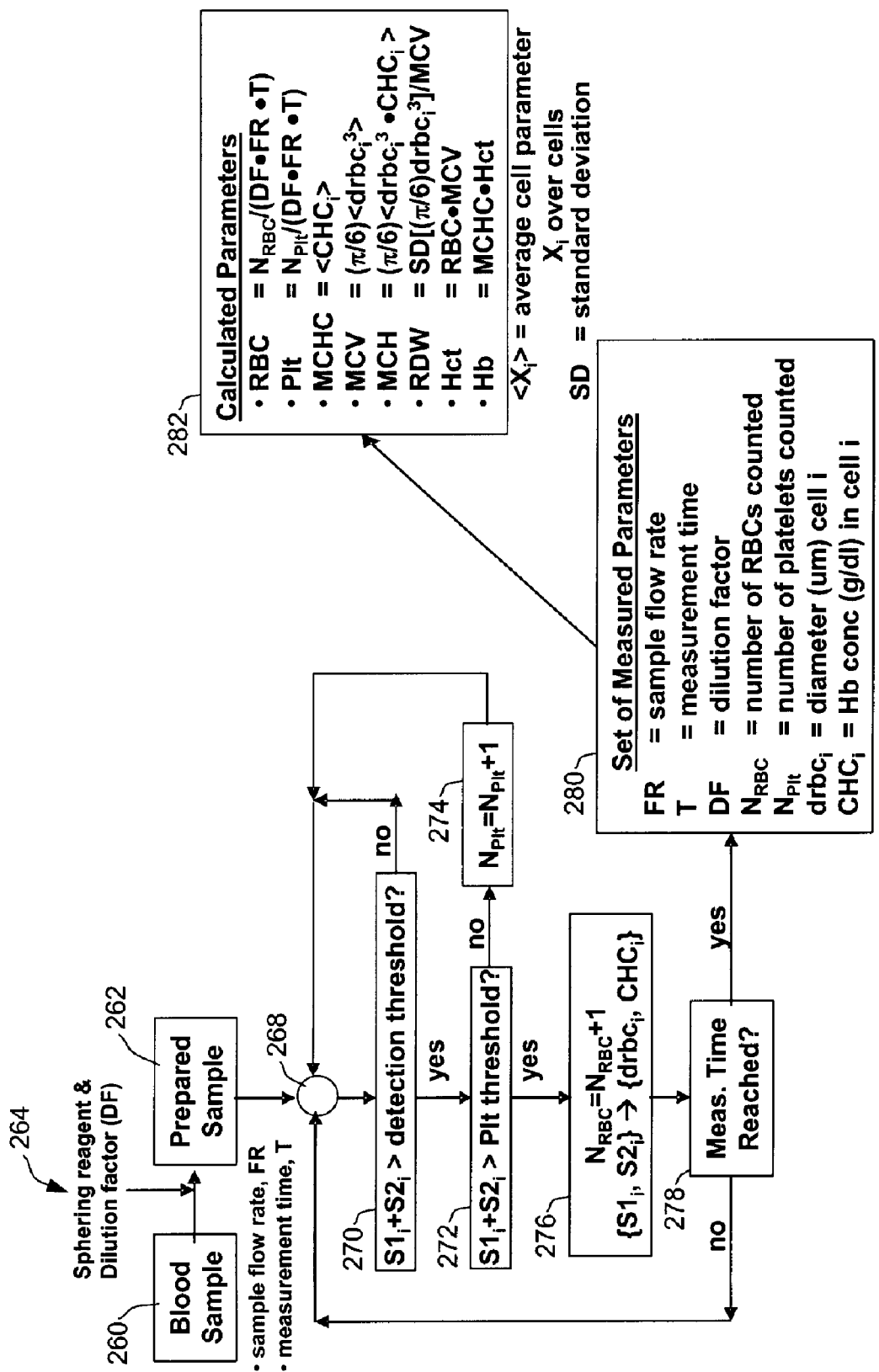
FIG. 7 is a flow diagram showing an illustrative method for obtaining a number of red blood cell parameters in accordance with the present invention.

FIG. 7 is a flow diagram showing an illustrative method for obtaining a number of red blood cell parameters in accordance with the present invention. In the illustrative method, a blood sample is acquired at step 260. Next, the blood sample is diluted to a desired Dilution Factor (DF), and sphered as shown at 264. The diluted and sphered blood cells are then hydrodynamically focused and provided single file down a RBC/P cytometry channel in the removable cartridge. A light source 216, such as a Vertical Cavity Surface Emitting Laser (VCSEL), shines light on the individual cells as they pass by an analysis region of the RBC/P cytometry channel. Some of the incident light provided by the VCSEL(s) is scattered, and a detector may be used to detect the scattered light. In some cases, the detector detects both Forward Angle Scatter Light (FALS) and Small Angle Scatter Light (SALS) for each cell. A processor or the like may then map the two independent scatter parameters, namely SALS and FALS, for each cell to a cell diameter parameter and a cell hemoglobin concentration parameter as follows:

$$\{S_{SALSi}, S_{FALSi}\} \rightarrow \{drbc_i, CHC_i\}$$

As shown at 270, if the intensity of the scatter $S_{SALSi}$ plus $S_{FALSi}$ is not greater than a predetermined detection threshold, control is passed back to step 268. However, if the intensity of the scatter $S_{SALSi}$ plus $S_{FALSi}$ is greater than a predetermined detection threshold, control is passed to step 272. Step 272 determines if the sum of $S_{SALSi}$ and $S_{FALSi}$ is greater than a predetermined platelet threshold. If the sum of $S_{SALSi}$ and $S_{FALSi}$ is not greater than the predetermined platelet threshold, it is determined that the particle "i" is a platelet, and control is passed to step 274. Step 274 increments the number of counted platelets ($N_{Plt}$) by one, and passes control back to step 268.

If the sum of $S_{SALSi}$ and $S_{FALSi}$ is greater than a predetermined platelet threshold, the cell is a red blood cell, and control is passed to step 276. Step 276 increments the number of counted red blood cells ($N_{RBC}$) by one, and passes control to step 278. Step 278 determines if a predetermined measurement time has been reached. If not, control is passed back to step 268.

Once the measurement time is reached at step 278, control is passed to step 280. Step 280 shows a number of measured parameters including, for example, sample flow rate (FR), measurement time (T) duration, sample dilution factor (DF), number of red blood cells counted ($N_{RBC}$), number of platelets counted ($N_{Plt}$), the diameter of each cell ($drbc_i$) and hemoglobin concentration of each cell ($CHC_i$). From these parameters, and as shown at step 282, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=<$CHC_i$>), a mean cell volume (MCV=($\pi$/6)×<$drbc_i^3$>), a mean cell hemoglobin content (MCH=($\pi$/6)×<$drbc_i^3$×$CHC_i$>), a relative distribution width (RDW=Standard Deviation of [($\pi$/6)×$drbc_i^3$]/MCV), a Hematocrit parameter (Hct=RBC×MCV) and/or a hemoglobin concentration (Hb=MCHC×Hct), wherein the notation <$X_i$> means the average cell parameter over all cells $X_i$.

FIG. 8 is a schematic flow diagram showing another illustrative method for analyzing a blood sample in accordance with the present invention. In this illustrative method, a blood sample is acquired, and provided to a blood sample reservoir, as shown at step 300. Next, the blood sample is provided to an anti-coagulant coated capillary in a removable cartridge, and diluted. The blood sample is then partitioned and provided to a Red Blood Cell and Platelet (RBC/P) measurement channel 304 and a White Blood Cell (WBC) measurement channel 340.

In the RBC/P measurement channel 304, the red blood cells are first sphered as shown at 306, and then hydrodynamically focused and provided single file down a RBC/P cytometry channel 308 in the removable cartridge. A first light source 310, such as a Vertical Cavity Surface Emitting Laser (VCSEL) and associated optics, provides a focused light beam on the individual cells as they pass by an analysis region of the RBC/P cytometry channel 308. In some cases, an array of VCSEL devices is provided, and only the VCSEL(s) that is/are aligned with the individual cells as they pass by an analysis region of the RBC/P cytometry channel 308 is/are activated.

As the individual cells/particles pass through the focused incident light beam, some of the light is blocked, scattered or otherwise obstructed, which can be detected by a detector (not shown). When two or more light sources are focused on different spaced spots along the RBC/P cytometry channel 308, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some embodiments, another light source 314 and associated optics may be provided by an analyzer. The associated optics of light source 314 may collimate the light, and measure off-axis scatter, such as SALS and FALS scatter. As noted above, the SALS and FALS scatter can be used to measure, for example, a number of red blood cells counted ($N_{RBC}$) 316, number of platelets counted ($N_{Plt}$) 322, the diameter of each cell ($drbc_i$), the cell volume 318, and hemoglobin concentration 320 of each cell ($CHC_i$). From these parameters, and as discussed above, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=<$CHC_i$>), a mean cell volume (MCV=($\pi/6$)× <$drbc_i^3$>), a mean cell hemoglobin content (MCH=($\pi/6$)× <$drbc_i^3 \times CHC_i$>), a relative distribution width (RDW=Standard Deviation of [($\pi/6$)×$drbc_i^3$]/MCV), a Hematocrit parameter (Hct=RBC×MCV) and/or a hemoglobin concentration (Hb=MCHC×Hct), wherein the notation <$X_i$> means the average cell parameter over all cells $X_i$.

In the illustrative WBC measurement channel 340, the red blood cells are lysed, and dye is injected as appropriate, as shown at 342. The cells are then hydrodynamically focused and provided single file down a WBC cytometry channel 344 in the removable cartridge. A light source 346, such as a Vertical Cavity Surface Emitting Laser (VCSEL), shines light on the individual cells as they pass by an analysis region of the WBC cytometry channel 344. In some cases, an array of VCSEL devices is provided, and only the VCSEL(s) that is/are aligned with the individual cells as they pass by the analysis region of the WBC cytometry channel 344 is activated.

As the individual cells/particles pass through the focused incident light beam, some of the light is blocked, scattered or otherwise obstructed, which can be detected by a detector (not shown). When two or more light sources are focused on different spaced spots along the WBC cytometry channel 344, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some embodiments, a light source 350 and associated optics and/or polarizers may be provided. The associated optics of light source 350 may collimate the light, and measure off-axis scatter, such as SALS, FALS and LALS scatter, as shown at 354. Like above, the SALS, FALS and LALS scatter can be used to measure, for example, the number of white blood cells counted ($N_{WBC}$) 352, as well as to help with white blood cell differentiation, as shown at 356. In some cases, one or more polarizers is/are provided to polarize the light provided by the light source, and the level of polarization extinction/rotation detected at the detector may be used to help perform white blood cell differentiation, but this is not required in all embodiments.

In the illustrative embodiment, the cells that exit the WBC cytometry channel 344 may be provided to a bulk absorption channel 360. A light source 362 may shine light onto the cells present in the absorption channel 360, and a detector 364 may detect the light that is not absorbed by the resident cells. The absorption channel 360 may thus be used to measure the bulk absorption level of the resident cells. The absorption level may provide, for example, a measure of the bulk or mean cell hemoglobin concentration in the blood sample.

Figure 9:
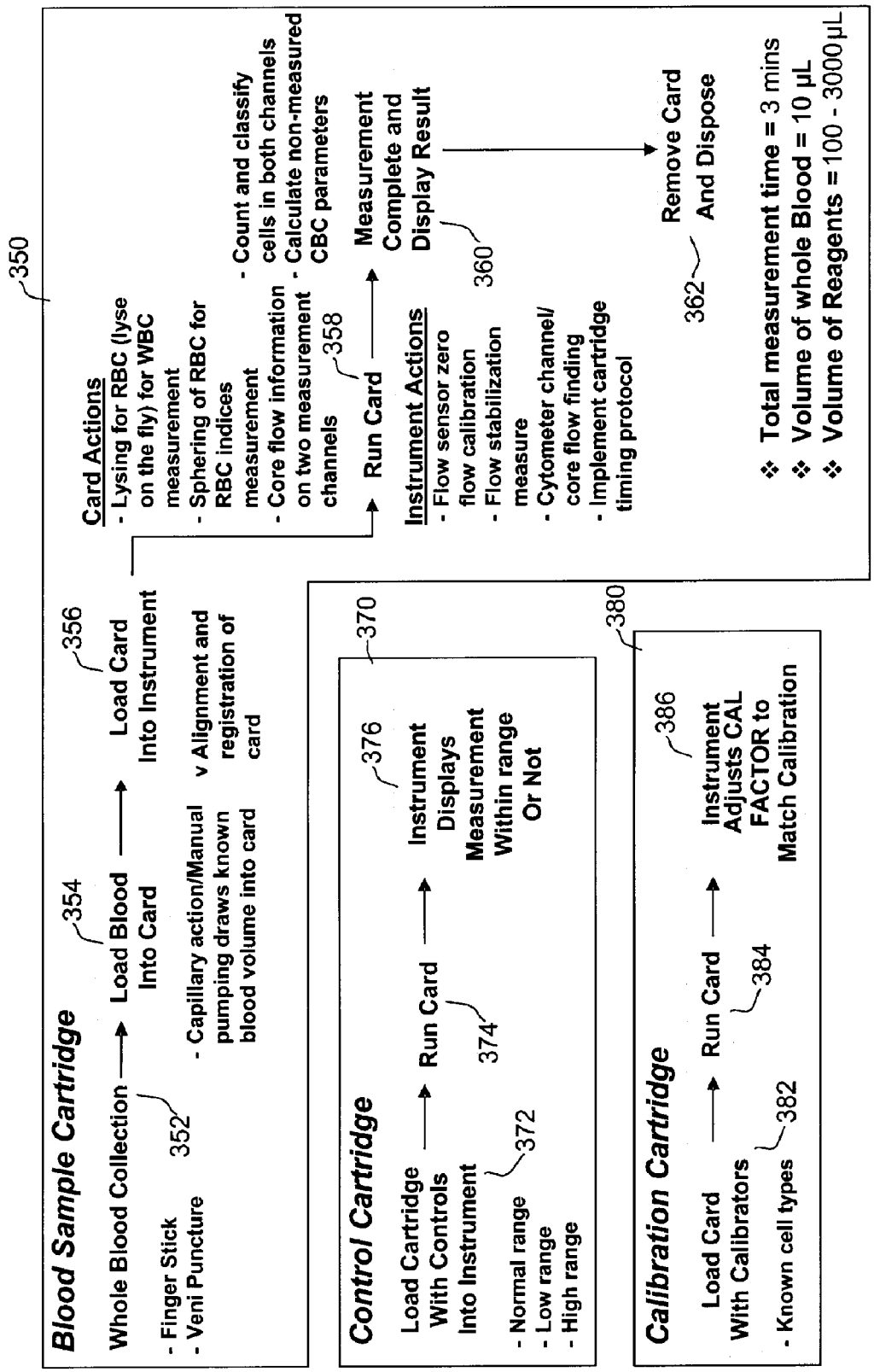
FIG. 9 is a schematic flow diagram showing an illustrative method for operating a sample analyzer in accordance with the present invention.

FIG. 9 is a schematic flow diagram showing an illustrative method for operating a sample analyzer in accordance with the present invention. In the illustrative embodiment, a blood analysis cartridge may be used and analyzed as shown at 350, a control cartridge may be used and analyzed to help verify the performance of the analyzer as shown at 370, and/or a calibration cartridge may be used and analyzed to help calibrate the analyzer as shown at 380. The blood analysis cartridge may be loaded each time a blood analysis is to be performed. The control cartridge may be loaded into the analyzer on a period basis, such as once a day, to verify that the analyzer is producing accurate results. The calibration cartridge may be loaded into the analyzer on a less frequent basis, such as once every three months, to recalibrate the analyzer.

Each cartridge may include all of the necessary fluids and/ or components to perform the corresponding function. As such, very little training may be needed to operate and/or maintain the analyzer, while still achieving accurate results. The ability to provide a sample analyzer with removable and/or disposable cartridges that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis.

When a blood analysis cartridge is used as shown at 350, a blood sample is collected and loaded into the blood analysis cartridge, as shown at 352 and 354. The blood sample may be drawing into the blood analysis cartridge by capillary action or manual pumping, as desired. The blood analysis cartridge may then be loaded into the analyzer instrument. In the illustrative embodiment, the analyzer may then self-align the blood analysis cartridge and the corresponding components (e.g. light sources/light detectors, etc.) of the analyzer, as shown at 356. Next, one or more buttons may be pushed to begin the blood analysis process. Rather than pushing a button or the like, and in some cases, the step of simply loading the cartridge into the analyzer may cause the analyzer to initiate the alignment and blood analysis process.

Once the analyzer is activated, the analyzer may perform a number of tests. For example, the analyzer may close all of the valves on the blood analysis card and apply pressure to the various fluid ports on the card. The analyzer may then measure the flow rate flowing past one or more flow sensors on the card. The flow should be zero, since all of the valves are closed. However, if the flow sensors indicate a non-zero flow rate, the analyzer may recalibrate the flow sensors back to a zero flow. This may help increase the accuracy of the flow sensor measurements. Alternatively, or in addition, the analyzer may check for blood clotting in the removable cartridge by, for example, measuring the flow rate of the blood sample (e.g. using a flow sensor) along with the pressure applied, and if the flow rate is too low relative to the applied pressure, determining that the blood sample has clotted. If blood clotting is detected, the analyzer may display a message that indicates that the measurement has failed.

The analyzer may then implement a blood analysis cartridge timing protocol. The blood analysis cartridge timing protocol may be similar to that shown and described in U.S. patent application Ser. No. 10/932,662, which is assigned to the assignee of the present invention and incorporated herein by reference. The particular blood analysis cartridge timing protocol may depend on the specific design of the blood analysis cartridge. The analyzer may also verify that there is a stable core flow in any cytometry channels on the blood analysis cartridge, and identify the location of the core flow if present.

The blood analysis cartridge may then, for example, lyse red blood cells in a portion of the blood sample that will be used for white blood cell measurements, sphere the red blood cells in a portion of the blood sample that will be used for red blood cell measurements, form core flows in any cytometry channels on the blood analysis cartridge, and/or perform any other desirable function. The analyzer may provide light to selected regions of the blood analysis cartridge, such as any cytometry channels, and detect light that passes through the selected regions.

From this, the analyzer may count and classify particles in the sample such as white blood cells, red blood cells, platelets, etc., and then display, print, produce a sound, or otherwise indicate a result of the blood analysis to a user. In some embodiments, the analyzer displays or prints out quantitative results (e.g. inside and/or outside of a predefined range), such that no further calculations or interpretation is required by the user. Finally, the blood analysis cartridge may be removed from the analyzer, and disposed of.

When a control run is to be performed as shown at 370, a control cartridge may be used. In some cases, a control run may be performed periodically, such as once a day or once a week. The control cartridge may include a control sample that has known characteristics. Thus, when an analysis is performed by the analyzer on the control sample, a known result should be achieved. In the illustrative method, a control cartridge is loaded into the analyzer, as shown at 372. Next, the analyzer is activated as shown at 374, and the analyzer performs an analysis and displays a result as shown at 376. In some embodiments, the analyzer displays or prints out quantitative results (e.g. inside and/or outside of a predefined range), such that no further calculations or interpretation is required by the user. Finally, the control cartridge may be removed from the analyzer, and disposed of. If the results of the control run are outside of a predefined range, it may be desirable to perform a calibration run, such as calibration run 380.

When a calibration run is to be performed as shown at 380, a calibration cartridge may be used. In some cases, a calibration run may be performed periodically, such as one a month, or as otherwise needed. The calibration cartridge may include a calibration sample with known characteristics. Thus, when an analysis is performed by the analyzer on the calibration sample, a known result should be achieved. In the illustrative method, a calibration cartridge is loaded into the analyzer, as shown at 382. Next, the analyzer is activated as shown at 384, and a number of results are obtained. By comparing the results obtained during the calibration run with expected results, the analyzer may automatically adjust one or more calibration factors in memory to recalibrate the analyzer so that, during a subsequent run, the analyzer will produce the expected or desired results, as shown at 386.

Figure 10:
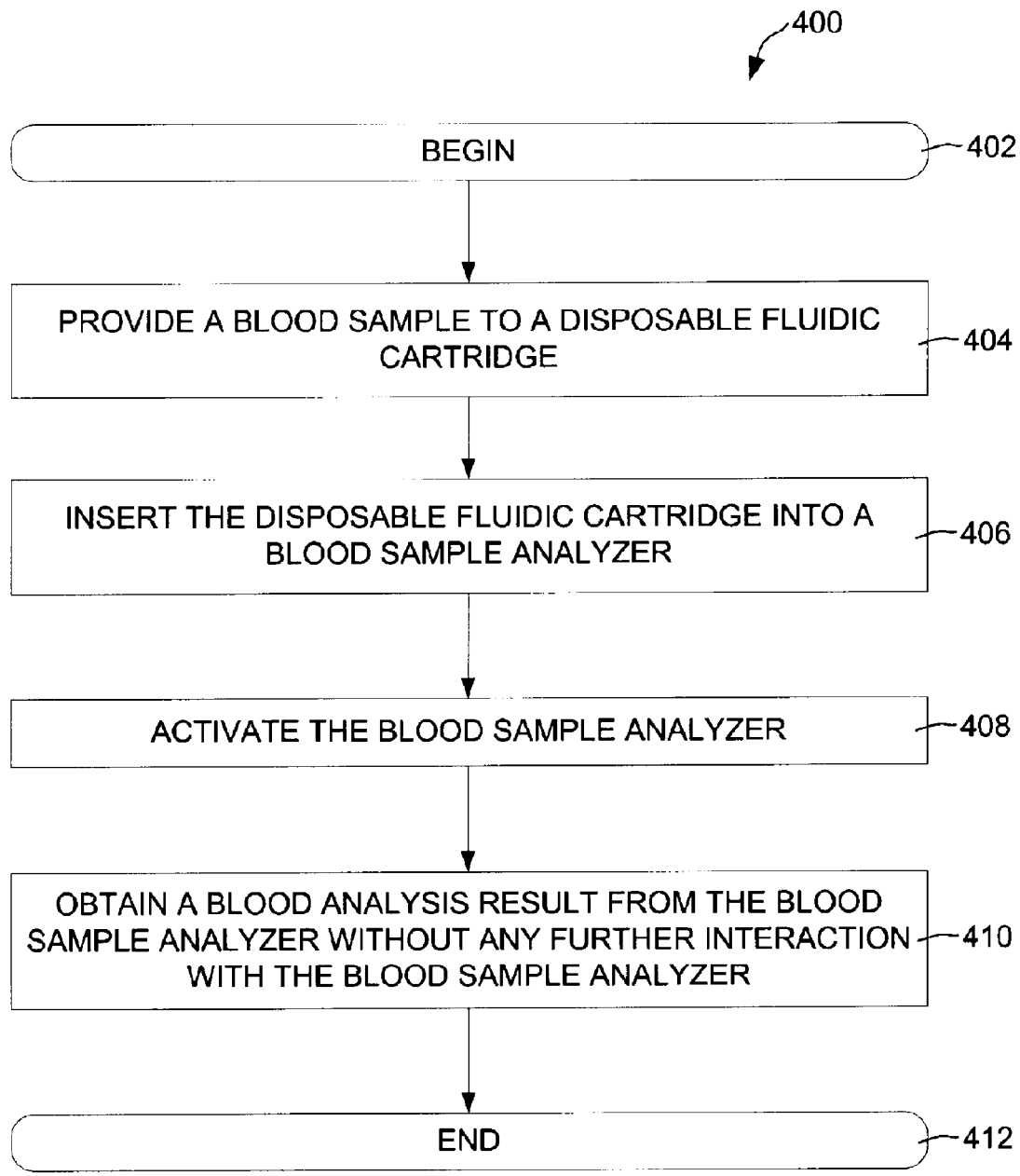
FIG. 10 is a flow diagram showing another illustrative method for operating a sample analyzer in accordance with the present invention.

FIG. 10 is a flow diagram showing another illustrative method for operating a sample analyzer in accordance with the present invention. The illustrative method is generally shown at 400, and is entered at step 402. Control is passed to step 404, wherein a blood sample is provided to a disposable fluidic cartridge. Control is then passed to step 406, wherein the disposable fluidic cartridge is inserted into a blood sample analyzer. Control is then passed to step 408. Step 408 activates the blood sample analyzer, and step 410 obtains a blood analysis result from the blood sample analyzer without any further interaction from the user of the blood sample analyzer. Control is then passed to step 412, wherein the method is exited.

Figure 11:
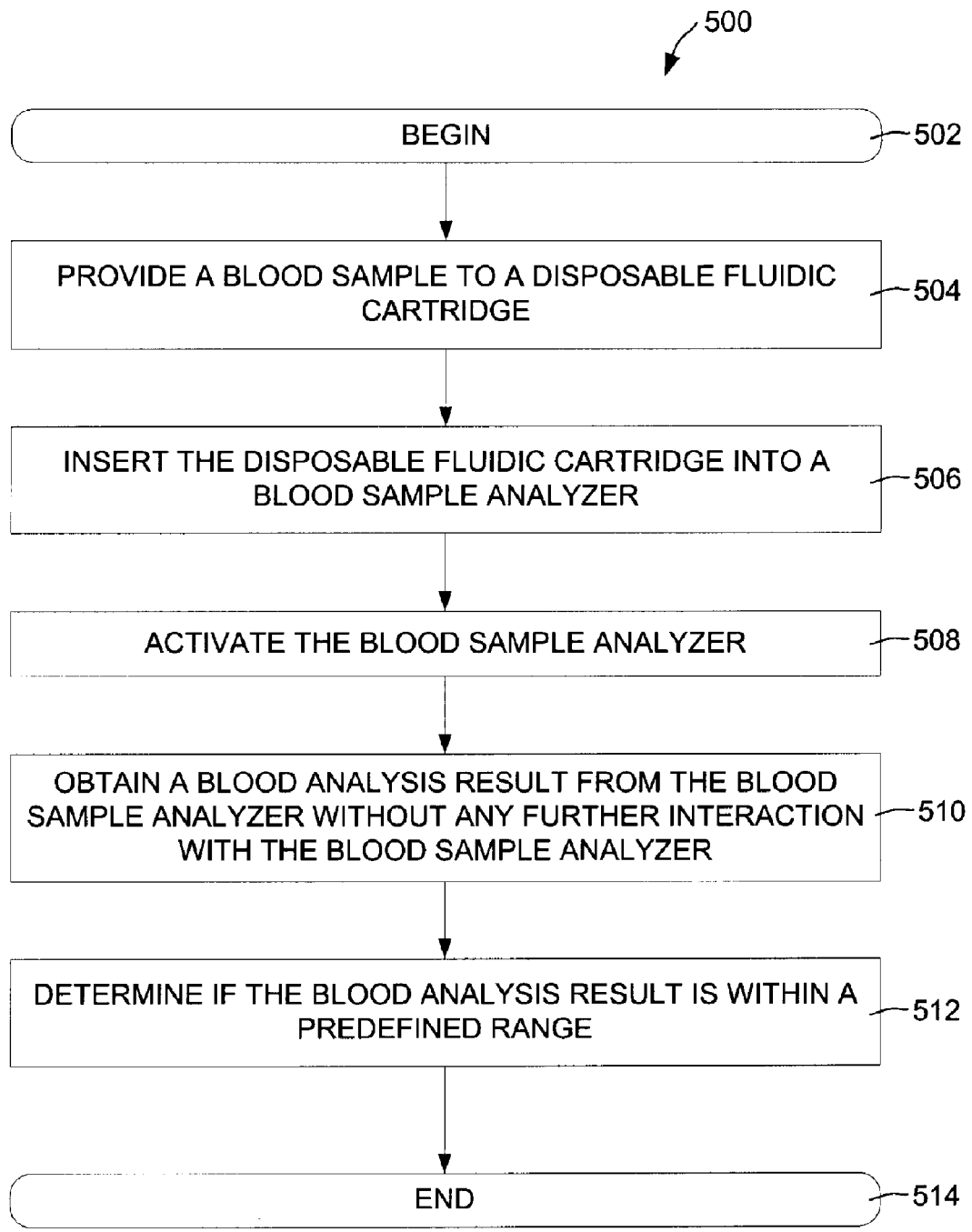
FIG. 11 is a flow diagram showing another illustrative method for operating a sample analyzer in accordance with the present invention.

FIG. 11 is a flow diagram showing another illustrative method for operating a sample analyzer in accordance with the present invention. The illustrative method is generally shown at 500, and begins at step 502. Control is passed to step 504, wherein a blood sample is provided to a disposable fluidic cartridge. Control is then passed to step 506, wherein the disposable fluidic cartridge is inserted into a blood sample analyzer. Control is then passed to step 508. Step 508 activates the blood sample analyzer, and step 510 obtains a blood analysis result from the blood sample analyzer without any further interaction from the user of the blood sample analyzer. Control is then passed to step 512. Step 512 determines if the blood analysis result is within a predefined range. As indicated above, and in some embodiments, the analyzer may display or print out quantitative results (e.g. inside and/or outside of a predefined range), such that no further calculations or interpretation is required by the user. Control is then passed to step 514, wherein the method is exited.

Figure 12:
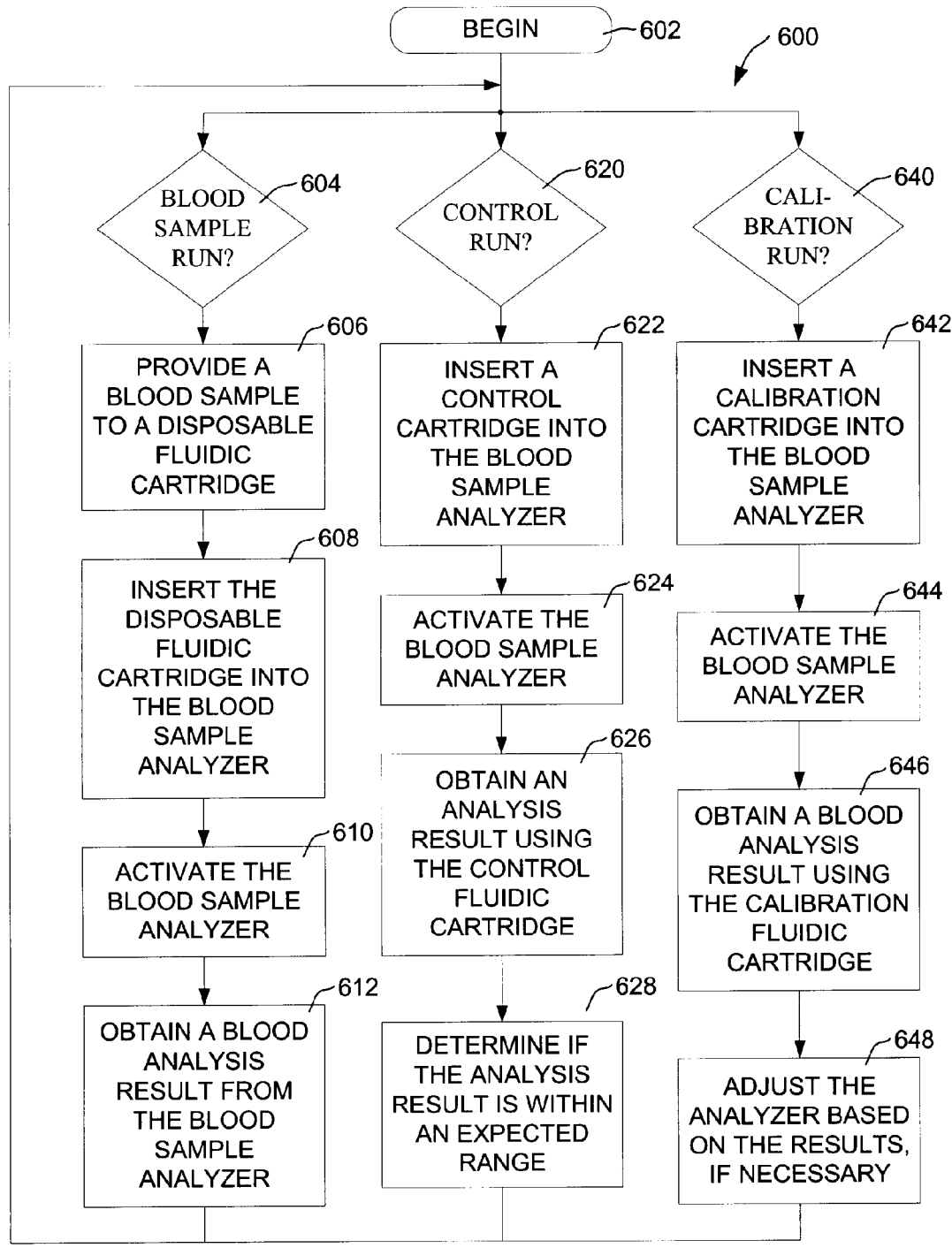
FIG. 12 is a flow diagram showing another illustrative method for operating a sample analyzer in accordance with the present invention.

FIG. 12 is a flow diagram showing another illustrative method for operating a sample analyzer in accordance with the present invention. The method is generally shown at 600, and is entered at step 602. In the illustrative method, a blood analysis cartridge may be used and analyzed as shown at 604, a control cartridge may be used and analyzed to help verify the performance of the analyzer as shown at 620, and/or a calibration cartridge may be used and analyzed to help calibrate the analyzer as shown at 640. The blood analysis cartridge may be loaded each time a blood analysis is to be performed. The control cartridge may be loaded into the analyzer on a period basis, such as once a day, to verify that the analyzer is producing accurate results. The calibration cartridge may be loaded into the analyzer on a less frequent basis, such as once every three months, to recalibrate the analyzer, or as otherwise needed.

Each cartridge type may include all of the necessary fluids and/or components to perform the corresponding function. As such, very little training may be needed to operate and/or maintain the analyzer, while still achieving accurate results. The ability to provide a sample analyzer with removable and/or disposable cartridges that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis.

In the illustrative method of FIG. 12, when a blood analysis cartridge is to be used, control is passed to step 604. At step 606, a blood sample is provided to a disposable fluidic cartridge. Control is then passed to step 608, wherein the disposable fluidic cartridge is inserted into the blood sample analyzer. Control is then passed to step 610. Step 610 activates the blood sample analyzer, and step 612 obtains the blood analysis result from the blood sample analyzer.

When a control cartridge is to be used, control is passed to step 620. Step 620 passes control to step 622, wherein a control cartridge is inserted into the blood sample analyzer. Control is then passed to step 624. Step 624 activates the blood sample analyzer, and step 626 obtains a control analysis result using the control fluidic cartridge. Control is then passed to step 628. Step 628 determines if the control analysis result is within an expected control range. If the control analysis result is not within an expected range, the results obtained for a blood analysis cartridge should not be trusted. In some cases, a calibration cartridge may be run to re-calibrate the sample analyzer, followed by another control cartridge to verify the operation/calibration of the sample analyzer.

When a calibration cartridge is to be used, control is passed to step 640. Step 640 passes control to step 642. Step 642 inserts a calibration cartridge into the blood sample analyzer. Control is then passed to step 644. Step 644 activates the blood sample analyzer, and step 646 obtains a calibration analysis result using the calibration fluidic cartridge. Control is then passed to step 648. Based on the calibration analysis results, step 648 adjusts the analyzer as necessary.

What is claimed is:

1. A disposable analysis cartridge capable of performing at least part of a blood sample measurement, comprising:
- two or more reagent storage reservoirs, a first one for storing a lysing reagent and a second one for storing a sphering reagent;
- a first flow sensor in fluid communication with the first one of the reagent storage reservoirs;
- a second flow sensor in fluid communication with the second one of the reagent storage reservoirs;
- a lysing on the fly channel in fluid communication with the first one of the reagent storage reservoirs;
- a sphering on the fly channel in fluid communication with the second one of the reagent storage reservoirs; and
- a first flow cytometry analysis channel structured to hydrodynamically focus a blood sample and to support flow cytometric measurements, the first flow cytometry analysis channel in fluid communication with and downstream of the lysing on the fly channel; and
- a second flow cytometry analysis channel structured to hydrodynamically focus a blood sample and to support flow cytometric measurements, the second flow cytometry analysis channel in fluid communication with and downstream of the sphering on the fly channel.

* * * * *